(12) United States Patent
Kikuzawa

(10) Patent No.: US 10,350,808 B2
(45) Date of Patent: Jul. 16, 2019

(54) FLEXIBLE TUBE AND PRODUCTION APPARATUS THEREFOR

(71) Applicant: PLA GIKEN CO., LTD., Osaka (JP)

(72) Inventor: Yoshiharu Kikuzawa, Osaka (JP)

(73) Assignee: PLA GIKEN CO., LTD., Osaka (JP)

(*) Notice: Subject to any disclaimer, the term of this patent is extended or adjusted under 35 U.S.C. 154(b) by 94 days.

(21) Appl. No.: 15/635,660

(22) Filed: Jun. 28, 2017

(65) Prior Publication Data

US 2017/0368733 A1 Dec. 28, 2017

Related U.S. Application Data

(63) Continuation of application No. PCT/JP2016/005256, filed on Dec. 28, 2016.

(30) Foreign Application Priority Data

Jun. 28, 2016 (JP) ................................. 2016-128003

(51) Int. Cl.
*B29C 47/02* (2006.01)
*B29C 47/20* (2006.01)
(Continued)

(52) U.S. Cl.
CPC ........... *B29C 48/30* (2019.02); *A61M 25/005* (2013.01); *A61M 25/0012* (2013.01);
(Continued)

(58) Field of Classification Search
CPC ............ B29C 47/0023; B29C 47/0026; B29C 47/021; B29C 47/025; B29C 47/06;
(Continued)

(56) References Cited

U.S. PATENT DOCUMENTS 3,359,357 A * 12/1967 Bentley, Jr. ........... B29C 47/021
264/171.12
3,697,632 A * 10/1972 Tenner .................... B29C 47/22
264/40.5
(Continued)

FOREIGN PATENT DOCUMENTS

EP 1757428 A1 2/2007
JP 02-280765 A 11/1990
(Continued)

OTHER PUBLICATIONS

Extended European Search Report dated Mar. 16, 2018 of European patent application No. 16876981.8.
(Continued)

*Primary Examiner* — Joseph S Del Sole
*Assistant Examiner* — Joseph S Leyson
(74) *Attorney, Agent, or Firm* — Renner, Otto, Boisselle & Sklar, LLP

(57) ABSTRACT

Provided is a production apparatus capable of producing a flexible tube whose hardness is naturally varied along the length direction thereof. This mixing valve includes: a first valve configured to distribute a first resin to a resin supply path and a resin discharge path; and a second valve configured to distribute a second resin to the resin supply path and the resin discharge path. In the mixing valve, the mixing proportion between the first resin and the second resin is increased or decreased in association with molding of the flexible tube, by changing a distribution ratio of the first resin in the first valve and a distribution ratio of the second resin in the second valve while keeping constant the total of the supply mounts of the first resin and the second resin supplied to a die.

6 Claims, 14 Drawing Sheets

(51) Int. Cl.
*B29C 47/28* (2006.01)
*B29C 47/92* (2006.01)
*B29C 48/30* (2019.01)
*B29C 48/335* (2019.01)
*B29C 48/10* (2019.01)
*B29C 48/151* (2019.01)
*B29C 48/49* (2019.01)
*B29C 48/32* (2019.01)
*A61M 25/00* (2006.01)
*B29C 48/92* (2019.01)
*B29C 48/09* (2019.01)
*B29C 48/18* (2019.01)
*B29C 48/25* (2019.01)
*B29C 48/34* (2019.01)
*B29L 31/00* (2006.01)
*B29L 23/00* (2006.01)

(52) U.S. Cl.
CPC .............. *B29C 48/09* (2019.02); *B29C 48/10* (2019.02); *B29C 48/151* (2019.02); *B29C 48/18* (2019.02); *B29C 48/2692* (2019.02); *B29C 48/304* (2019.02); *B29C 48/32* (2019.02); *B29C 48/338* (2019.02); *B29C 48/34* (2019.02); *B29C 48/49* (2019.02); *B29C 48/92* (2019.02); *B29C 2948/926* (2019.02); *B29C 2948/92723* (2019.02); *B29C 2948/92828* (2019.02); *B29C 2948/92904* (2019.02); *B29C 2948/92942* (2019.02); *B29K 2995/002* (2013.01); *B29K 2995/007* (2013.01); *B29L 2023/00* (2013.01); *B29L 2031/7542* (2013.01); *B29L 2031/7546* (2013.01)

(58) Field of Classification Search
CPC ... B29C 47/0816; B29C 47/128; B29C 47/28; B29C 48/09; B29C 48/10; B29C 48/151; B29C 48/2556; B29C 48/30; B29C 48/304; B29C 48/32; B29C 48/34; B29C 48/49; B29C 48/92; B29C 2948/926; B29C 2948/92723; B29C 2948/92904; B29C 2948/92942; A61M 25/0012; A61M 25/005
See application file for complete search history.

(56) References Cited

U.S. PATENT DOCUMENTS

| | | | |
|---|---|---|---|
| 3,752,617 A | | 8/1973 | Burlis et al. |
| 4,164,956 A | * | 8/1979 | Takahashi ............... B29B 7/801 137/242 |
| 5,542,937 A | * | 8/1996 | Chee ................. A61M 25/0009 604/523 |
| 6,030,371 A | | 2/2000 | Pursley |
| 6,808,380 B1 | | 10/2004 | Watanabe et al. |
| 7,329,113 B2 | * | 2/2008 | Leseman ................ B21C 25/08 425/191 |

FOREIGN PATENT DOCUMENTS

| | | |
|---|---|---|
| JP | 05-023398 A | 2/1993 |
| JP | 08-057035 A | 3/1996 |
| JP | 2001-269411 A | 2/2001 |
| JP | 2001-293770 A | 10/2001 |
| JP | 2009-078369 A | 4/2009 |
| WO | 96/00100 A1 | 1/1996 |
| WO | 02/085440 A2 | 10/2002 |

OTHER PUBLICATIONS

International Search Report for corresponding International Application No. PCT/JP2016/005256 dated Feb. 7, 2017.
Form PCT/ISA/237 for corresponding International Application No. PCT/JP2016/005256 dated Feb. 7, 2017.

* cited by examiner

FLEXIBLE TUBE AND PRODUCTION APPARATUS THEREFOR

CROSS-REFERENCE TO RELATED APPLICATION

This application is a Continuation of International Application No. PCT/JP2016/005256, filed on Dec. 28, 2016, which in turn claims the benefit of Japanese Application No. 2016-128003 filed on Jun. 28, 2016, the disclosures of which Applications are incorporated by reference herein.

BACKGROUND

Field

The present invention relates to a flexible tube in which the outer face of a blade is covered with a resin, and relates to a production apparatus therefor.

Description of the Related Art

In medical institutions, in order to inject a drug solution, a contrast medium, or the like to a predetermined site in the living body of a patient, or in order to take out body fluid or the like from the living body, a tube-shaped medical instrument called a catheter is used. Since the catheter is inserted into the living body through a winding blood vessel or the like, the leading end portion to be inserted of the catheter is required to have flexibility so as to easily bend along the winding portion of the blood vessel or the like, without damaging the blood vessel or the like. Meanwhile, the portion, of the catheter, that is not inserted into the living body is required to have moderate rigidity so as to facilitate operation of the catheter. Thus, various kinds of catheters have been proposed whose hardness is varied stepwise along the length direction thereof such that the leading end portion is soft and the proximal end side is hard.

FIG. 19 is a schematic drawing of processes showing a general production method for producing a catheter shaft whose hardness is varied stepwise along the length direction. It should be noted that a catheter shaft denotes not the finished article of a catheter but an article from which a tube that is to be finished as a catheter is not yet cut out.

First, as shown in (a) of FIG. 19, a blade wire 80 is prepared in which, on the surface of a metal core wire 81, a resin inner layer tube 82 and a blade 83 which is obtained by weaving a thin metal wire into a tubular shape are provided in this order. Next, as shown in (b) of FIG. 19, resin outer layer tubes 84a to 84c each separately molded are mounted on the outer face of the blade wire 80. The outer layer tubes 84a to 84c are formed by extrusion-molding resins having different hardnesses, respectively, and for example, the hardness is increased in the order of the outer layer tube 84a, the outer layer tube 84b, and the outer layer tube 84c.

Next, as shown in (c) of FIG. 19, the blade wire 80 having the outer layer tubes 84a to 84c incorporated therewith is inserted into a shrinkable tube 85 which is made of resin and which is separately molded. The shrinkable tube 85 is a tube formed by extrusion-molding a resin material that shrinks by heating, and then subjected to reheating so as to have an expand diameter. Next, as shown in (d) of FIG. 19, in a state where the blade wire having the outer layer tubes 84a to 84c incorporated therewith is inserted in the shrinkable tube 85, the entirety thereof is uniformly heated to shrink so as to have dimensions that are close to the dimensions at the time of molding of the shrinkable tube 85 (i.e., close to the dimensions before the diameter was expanded through reheating). The outer layer tubes 84a to 84c melt in the shrinkable tube 85 to be a single tube, and come into close contact with the blade 83 and the inner layer tube 82.

Then, the shrinkable tube 85 is peeled off and the core wire 81 is pulled out, whereby one catheter shaft 86 is completed.

According to the production method shown in FIG. 19, the outer layer tubes 84a to 84c respectively molded in advance and having different hardnesses are integrated with one another by use of the shrinkable tube 85, whereby a catheter shaft is obtained whose hardness is varied in three levels along the length direction. However, the production method shown in FIG. 19 has a problem that the numbers of steps and production apparatuses that are required are large. An example of a technology that solves this problem is the technology described in Japanese Patent No. 5088818.

The extrusion molding apparatus described in Japanese Patent No. 5088818 forms a catheter shaft through extrusion molding, by directly extruding a resin onto the surface of a blade wire in which an inner layer tube and a blade are provided on the surface of a core wire. This extrusion molding apparatus includes: three extruders which melt and extrude resins having different hardnesses, respectively; a die which extrudes onto the surface of a blade wire the resins supplied from the respective extruder; and three open/close valves capable of opening/closing middle portions of three resin passages that allow the respective extruders and the die to be communicated with each other. The extrusion molding apparatus described in Japanese Patent No. 5088818 perform is extrusion molding while the open/close valves are sequentially opened/closed so as to switch the kinds of the resins supplied from the three extruders. According to this extrusion molding apparatus, a catheter shaft whose hardness is varied stepwise along the longitudinal direction thereof can be produced through a single extrusion molding step. Thus, compared with the production method shown in FIG. 19, the numbers of steps and production apparatuses that are required can be significantly reduced.

In the extrusion molding apparatus described in Japanese Patent No. 5088818, the hardness of the catheter shaft is varied stepwise by switching the kind of the resin to be supplied to the die. Thus, a portion that has been extrusion-molded with a single kind of resin has a constant hardness, and the hardness sharply changes before and after the switching of the kind of the resin supplied to the die. Thus, it is more preferable that the hardness is varied not stepwise but more naturally along the length direction of the catheter.

SUMMARY

Therefore, an object of the present invention is to provide a flexible tube production apparatus capable of producing a flexible tube whose hardness is naturally varied along the length direction thereof. Another object of the present invention is to provide a flexible tube whose hardness is naturally varied along the length direction thereof.

The present invention relates to a flexible tube production apparatus configured to mold a flexible tube by extruding a resin on a surface of a raw material tube. The flexible tube production apparatus according to the present invention includes: a die that has an insertion hole through which the raw material tube is inserted, and an extrusion hole through which a resin is extruded onto the raw material tube passing through the insertion hole; a first extruder configured to eject a first resin at a constant speed; a second extruder configured to eject a second resin different from the first resin at a constant speed; and a mixing valve that has a resin supply path for supplying a resin to the die and a resin discharge path for discharging the resin to outside. The mixing valve is capable of mixing the resins ejected from the first extruder and from the second extruder and supplying the resultant resin to the die through the resin supply path. The mixing valve includes: a first valve configured to distribute the first resin supplied from the first extruder, to the resin supply path and the resin discharge path; and a second valve configured to distribute the second resin supplied from the second extruder, to the resin supply path and the resin discharge path, and the mixing valve increases or decreases a mixing proportion between the first resin and the second resin in association with molding of the flexible tube, by changing a distribution ratio of the first resin in the first valve and a distribution ratio of the second resin in the second valve while keeping at a constant amount a total of a supply mount of the first resin from the first valve to the resin supply path and a supply mount of the second resin from the second valve to the resin supply path.

In addition, the present invention relates to a flexible tube production apparatus configured to mold a flexible tube by extruding a resin on a surface of a raw material tube. The flexible tube production apparatus according to the present invention includes: a die that has an insertion hole through which the raw material tube is inserted, and an extrusion hole through which a resin is extruded onto the raw material tube passing through the insertion hole; a first extruder configured to eject a first resin at a constant speed; a second extruder configured to eject a second resin different from the first resin at a constant speed; and a mixing valve that has a resin supply path for supplying a resin to the die and a resin discharge path for discharging the resin to outside. The mixing valve is capable of mixing the resins ejected from the first extruder and from the second extruder and supplying the resultant resin to the die through the resin supply path. The mixing valve includes: a first valve configured to distribute the first resin supplied from the first extruder, to the resin supply path and the resin discharge path; and a second valve configured to distribute the second resin supplied from the second extruder, to the resin supply path and the resin discharge path, and the mixing valve increases or decreases a mixing proportion between the first resin and the second resin in association with molding of the catheter shaft, by changing a distribution ratio of the first resin in the first valve and a distribution ratio of the second resin in the second valve while increasing or decreasing a total of a supply mount of the first resin from the first valve to the resin supply path and a supply mount of the second resin from the second valve to the resin supply path.

In addition, the present invention relates to a flexible tube in which a surface of a blade is covered with a resin layer, wherein the resin layer is formed from two kinds of resins that are different from each other, and a mixing ratio between the two kinds of resins forming the resin layer is continuously varied from one end of the flexible tube toward the other end thereof.

According to the present invention, a flexible tube production apparatus capable of producing a flexible tube whose hardness is naturally varied in the length direction can be provided. In addition, according to the present invention, a flexible tube whose hardness is naturally varied along the length direction can be provided.

DETAILED DESCRIPTION

Hereinafter, embodiments will be described in detail with reference to the drawings as appropriate. However, descriptions more detailed than necessary may be omitted. For example, detailed description of already well known matters or description of substantially identical configurations may be omitted. This is intended to avoid redundancy in the description below, and to facilitate understanding of those skilled in the art.

It should be noted that the inventor provide the attached drawings and the following description so that those skilled in the art can fully understand this disclosure. Therefore, the drawings and description are not intended to limit the subject defined by the claims.

Hereinafter, embodiments of the present invention are described. In the following, an example is described in which the present invention is applied to a production apparatus for a catheter shaft that is formed by extrusion-molding a resin onto the surface of a blade (net tube). However, the catheter shaft is merely an example of the flexible tube, and the present invention can be applied to a production apparatus for a flexible tube having another usage.

First Embodiment

<Overall Configuration of Catheter Shaft Production Apparatus>

Figure 1:
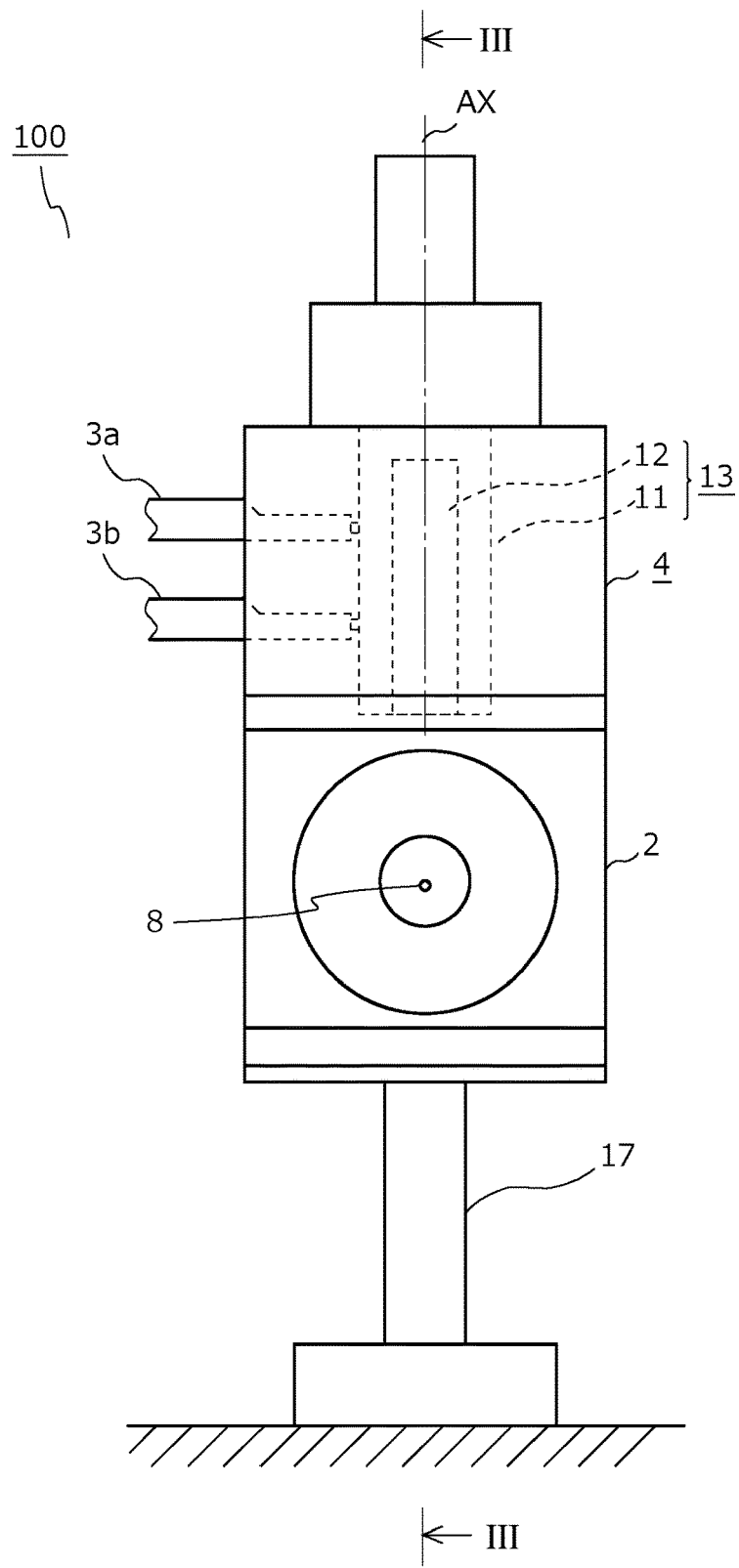
FIG. 1 is a front view of a catheter shaft production apparatus according to a first embodiment.
Figure 2:
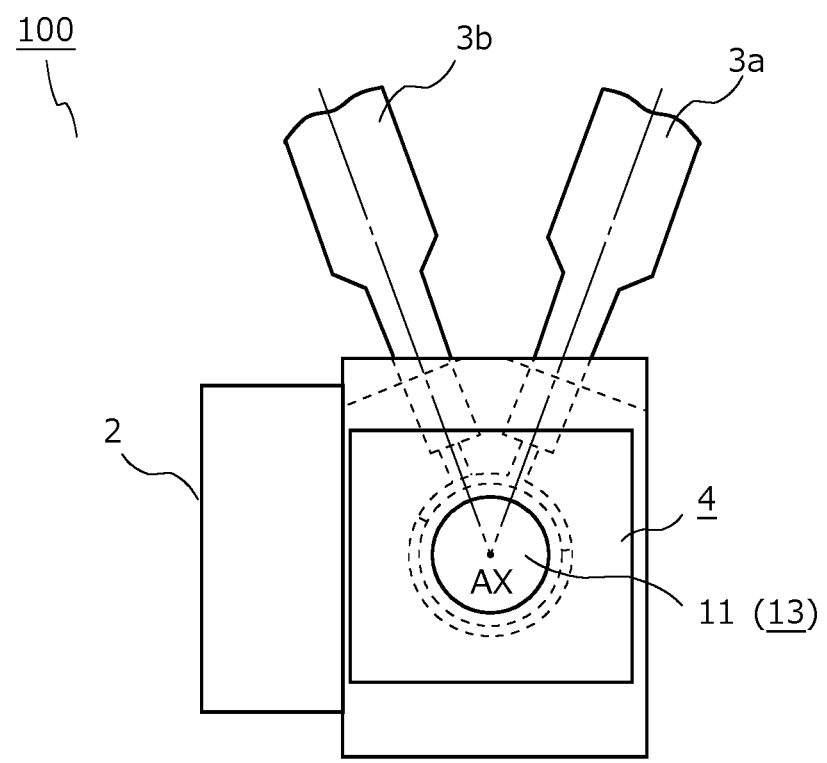
FIG. 2 is a top view of the catheter shaft production apparatus shown in FIG. 1.

FIG. 1 is a front view of a catheter shaft production apparatus according to an embodiment. FIG. 2 is a top view of the catheter shaft production apparatus shown in FIG. 1, and FIG. 3 is a cross-sectional view thereof, taken along the line III-III shown in FIG. 1.

A catheter shaft production apparatus 100 includes a die 2, a first extruder 3a, a second extruder 3b, and a mixing valve 4. The catheter shaft production apparatus 100 is fixed to a predetermined mounting base or the like with a pedestal 17 interposed therebetween. Although not shown, a supply device for supplying a blade wire 5 to the catheter shaft production apparatus 100, a haul-off device for hauling off a catheter shaft 6 that has been extrusion-molded, and the like are provided as appropriate at the upstream side and the downstream side of the catheter shaft production apparatus 100.

Figure 3:
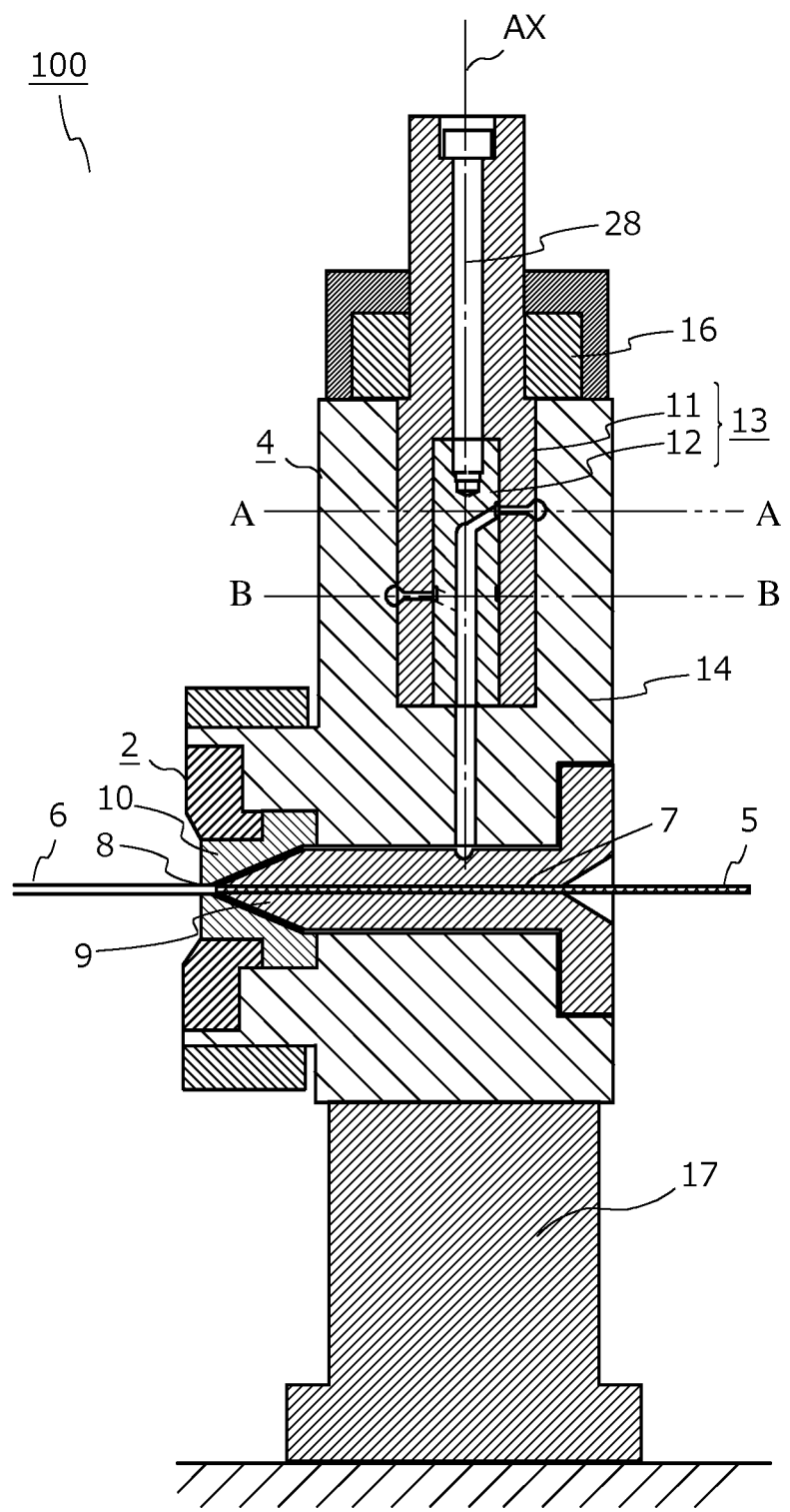
FIG. 3 is a cross-sectional view taken along a line shown in FIG. 1.

As shown in FIG. 3, the die 2 includes: an inner mold 9 provided with an insertion hole 7 into which a blade wire 5 is to be inserted; and an outer mold 10. Between the outer face of the inner mold 9 and the inner face of the outer mold 10, a gap for allowing a resin to flow therethrough is provided. While the blade wire 5 inserted in the insertion hole 7 is being advanced, the resin supplied into this gap is extruded from an extrusion hole 8 of the outer mold 10, whereby the catheter shaft 6 in which the outer face of the blade wire 5 is covered with the resin is molded.

Each of the first extruder 3a and the second extruder 3b, which are screw extruders, for example, melts pellets of a resin and extrudes at a constant speed the melted resin from an outlet at the leading end thereof. The first extruder 3a and the second extruder 3b are supplied with different resins, respectively. The melted resins respectively ejected from the first extruder 3a and the second extruder 3b are supplied to the mixing valve 4 described later, mixed at a predetermined mixing ratio in the mixing valve 4, and then, supplied to the die 2. In the present embodiment, as shown in FIG. 2, the first extruder 3a and the second extruder 3b are disposed such that the ejection axis of the first extruder 3a and the ejection axis of the second extruder 3b form an acute angle, whereby the space necessary for disposing the first extruder 3a and the second extruder 3b is reduced. However, the arrangement of the first extruder 3a and the second extruder 3b are not limited to the example shown in FIG. 2, and may be any arrangement. For example, the first extruder 3a and the second extruder 3b may be disposed such that the ejection axes thereof are orthogonal to each other, or the first extruder 3a and the second extruder 3b may be disposed so as to be opposed to each other.

The mixing valve 4 mixes two kinds of resins extruded from the first extruder 3a and the second extruder 3b and supplies the resultant resin to the die 2. The mixing valve 4 according to the present embodiment includes: a valve body 13 having a columnar shape and rotatable about an axis AX; and a valve case 14 which houses the valve body 13 such that the valve body 13 is rotatable therein. As shown in FIG. 3, the valve body 13 is composed of: a hollow first cylinder 11; a second cylinder 12 housed in the first cylinder 11; and a shaft body 28 which fixes the first cylinder 11 and the second cylinder 12 together. Details of the first cylinder 11 and the second cylinder 12 are described later. A space having a columnar shape that is substantially the same as an outer shape of the valve body is provided in the valve case 14. The valve body 13 is accommodated in this space. In a state where the valve body 13 is housed in the valve case 14, the valve body 13 is rotatable about the axis AX, with the outer peripheral surface of the valve body 13 sliding relative to the inner peripheral surface of the valve case 14.

As shown in FIG. 3, a drive mechanism 16 such as an actuator is provided above the valve case 14. The drive mechanism 16 is connected to the valve body 13, and rotates the valve body 13 about the axis AX in accordance with control of a control device not shown.

<Details of Configuration of Mixing Valve>

Hereinafter, details of the configuration of the mixing valve 4 are described.

Figure 4:
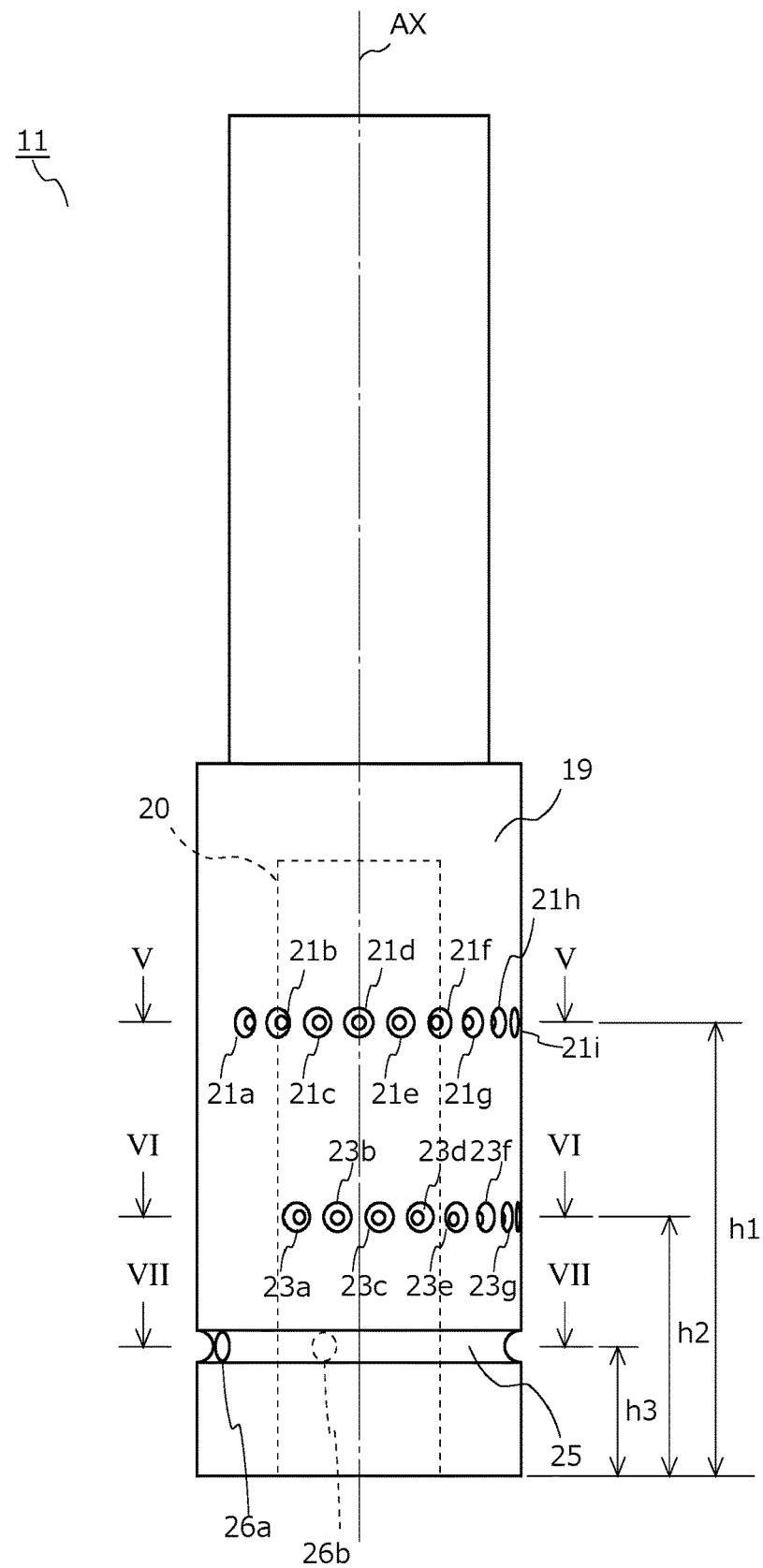
FIG. 4 is a front view of a first cylinder shown in FIG. 3.
Figure 5:
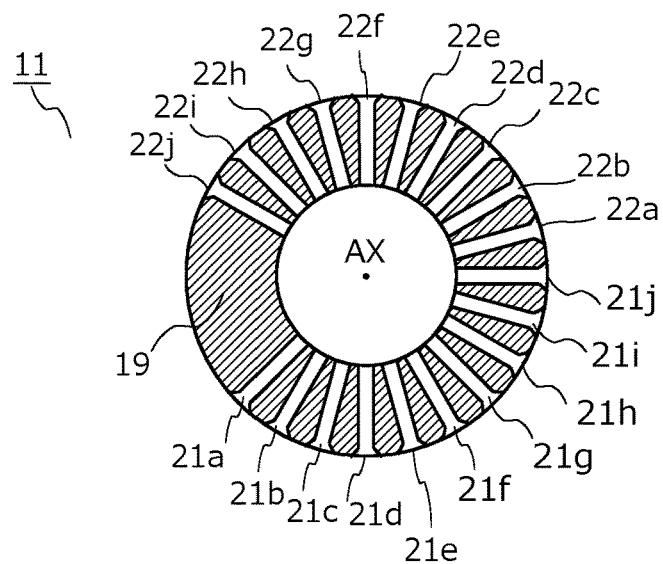
FIG. 5 is a cross-sectional view taken along a line V-V shown in FIG. 4.
Figure 6:
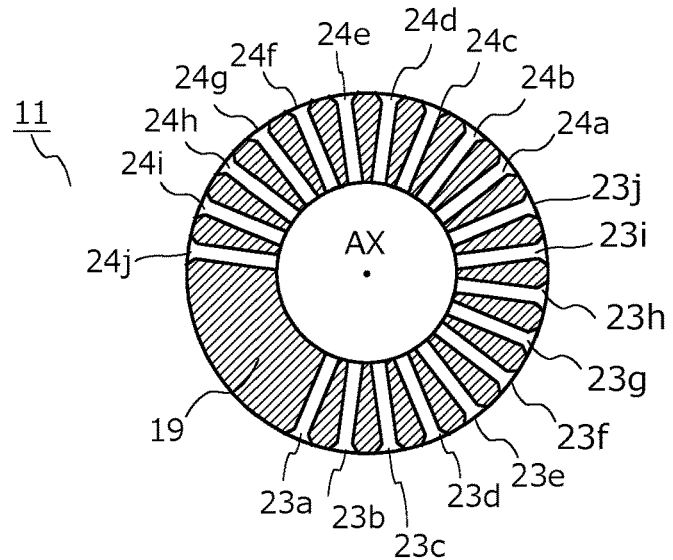
FIG. 6 is a cross-sectional view taken along a line VI-VI shown in FIG. 4.
Figure 7:
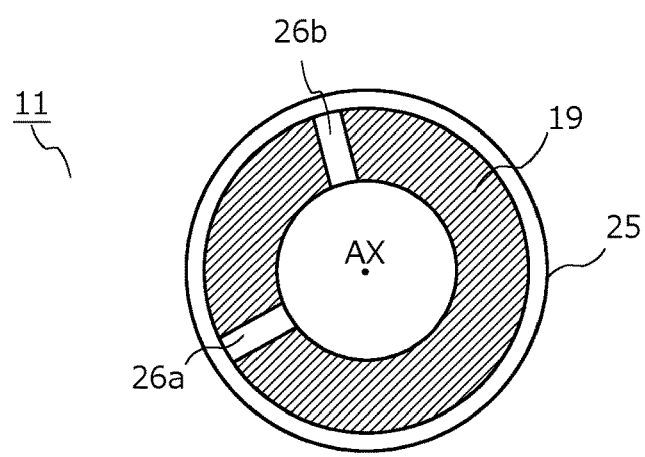
FIG. 7 is a cross-sectional view taken along a line VII-VII shown in FIG. 4.

FIG. 4 is a front view of the first cylinder shown in FIG. 3. FIG. 5 is a cross-sectional view taken along the line V-V shown in FIG. 4, FIG. 6 is a cross-sectional view taken along the line VI-VI shown in FIG. 4, and FIG. 7 is a cross-sectional view taken along the line VII-VII shown in FIG. 4.

The first cylinder 11 is a member that has a cylindrical shape whose one end (lower end in FIG. 4) is open and whose other end is closed. A space 20 having a columnar shape that is substantially the same as the outer shape of the second cylinder 12 is provided inside the first cylinder 11, whereby a peripheral wall portion 19 is formed. The first cylinder 11 is formed by cutting a metal, for example.

The first cylinder 11 is provided with a plurality of through-holes 21a to 21j, 22a to 22j, 23a to 23j, and 24a to 24j which each penetrate the peripheral wall portion 19 in radial directions.

As shown in FIGS. 4 and 5, the through-holes 21a to 21j and 22a to 22j each have an identical shape and an identical inner diameter, and are provided at a constant pitch in the circumferential direction of the first cylinder 11 such that the respective central axes are located at a height h1 from the lower end of the first cylinder 11, and such that the respective central axes form a constant angle therebetween. These through-holes 21a to 21j and 22a to 22j are supplied with the resin ejected from the first extruder 3a (hereinafter, referred to as "resin A"). The opening formed in the outer peripheral surface of the peripheral wall portion 19 by providing each of the through-holes 21a to 21j and 22a to 22j corresponds to a "first opening".

As shown in FIGS. 4 and 6, the through-holes 23a to 23j and 24a to 24j each have an identical shape and an identical inner diameter to those of the through-holes 21a to 21j and 22a to 22j, and are provided at a constant pitch in the circumferential direction of the first cylinder 11 such that the respective central axes are located at a height h2 from the lower end of the first cylinder 11, and such that the respective central axes form a constant angle therebetween. These through-holes 23a to 23j and 24a to 24j are supplied with the resin ejected from the second extruder 3b (hereinafter, referred to as "resin B"). The opening formed in the outer peripheral surface of the peripheral wall portion 19 by providing each of the through-holes 23a to 23j and 24a to 24j corresponds to a "second opening".

Further, as shown in FIGS. 4 and 7, a discharge groove 25 having a width in the up-down direction relative to the position at a height h3 from the lower end of the first cylinder 11 is formed in the outer peripheral surface of the first cylinder 11. In addition, through-holes 26a and 26b penetrating the peripheral wall portion 19 in radial directions of the first cylinder 11 are formed in the discharge groove 25. The discharge grooves 25 and the through-holes 26a and 26b are used in order to discharge (discard), to the outside, unnecessary resins that are not supplied to the die.

Figure 8:
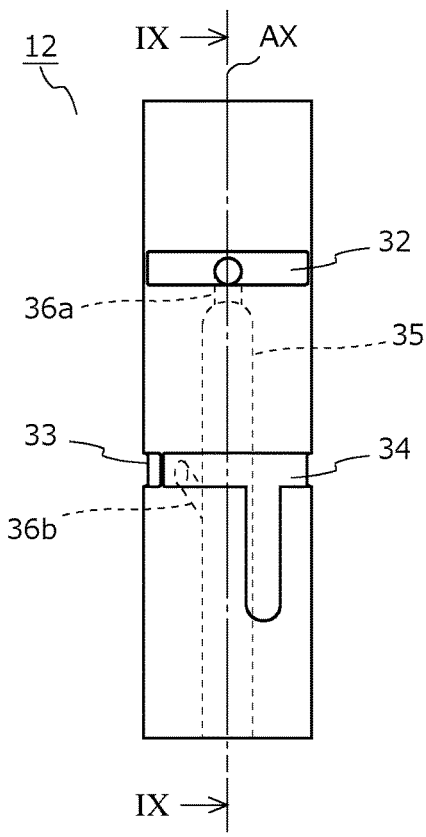
FIG. 8 is a front view of a second cylinder shown in FIG. 3.
Figure 9:
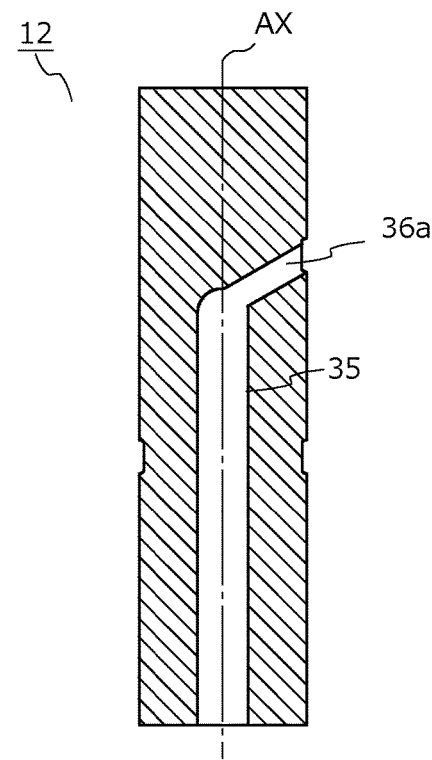
FIG. 9 is a cross-sectional view taken along a line IX-IX shown in FIG. 8.
Figure 10:
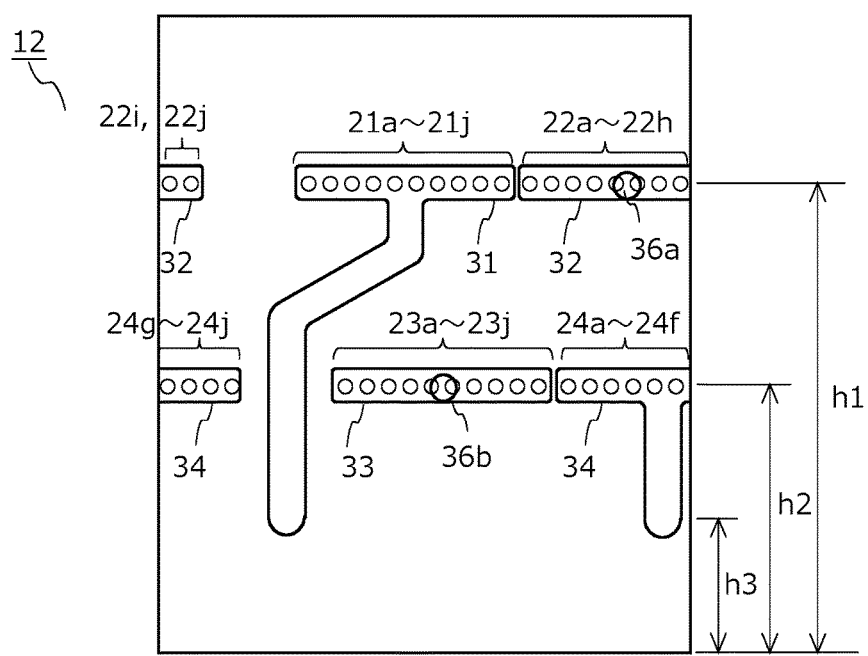
FIG. 10 is a development of the outer face of the second cylinder shown in FIG. 8.

FIG. 8 is a front view of the second cylinder shown in FIG. 3, FIG. 9 is a cross-sectional view taken along the line IX-IX shown in FIG. 8, and FIG. 10 is a development of the outer face of the second cylinder shown in FIG. 8. In FIG. 10, small circles are drawn with thin lines in grooves 31 to 34, but these circles do not denote structures provided in the second cylinder 12, but denote the positions to which inner-side openings of the through-holes 21a to 21j, 22a to 22*j*, 23*a* to 23*j*, and 24*a* to 24*j* provided in the first cylinder 11 are opposed when the second cylinder 12 is inserted in the first cylinder 11.

The second cylinder 12 is a member that has a substantially columnar shape. As shown in FIGS. 8 and 9, inside the second cylinder 12, a long hole 35 is provided which extends from one end (lower end in FIG. 8) along the central axis thereof to a predetermined height. The long hole 35 functions as a resin supply path for supplying the resin to the die. In addition, as shown in FIGS. 8 and 10, the plurality of grooves 31 to 34 are provided in the outer peripheral surface of the second cylinder 12. Further, as shown in FIGS. 8 to 10, the second cylinder 12 is provided with a flow-in path 36*a* which extends from a portion within the groove 32 to the long hole 35, and a flow-in path 36*b* which extends from a portion within the groove 33 to the long hole 35. The flow-in path 36*a* is a flow path for sending the resin A supplied to the groove 32, into the long hole 35. The flow-in path 36*b* is a flow path for sending the resin B supplied to the groove 33, into the long hole 35. The second cylinder 12 is also formed by cutting a metal, for example.

The groove 31 has: a portion that has a width in the up-down direction relative to the level of the height h1 from the lower end of the second cylinder 12, and that extends in the circumferential direction of the second cylinder 12; and a portion that extends in the axial direction of the second cylinder 12, and that reaches the position at the height h3 from the lower end of the second cylinder 12. In a state where the second cylinder 12 is inserted in the space 20 inside the first cylinder 11, as shown in FIG. 10, the inner-side openings of the through-holes 21*a* to 21*j* of the first cylinder 11 are opposed to the portion, of the groove 31, that extends in the circumferential direction. The lower end of the portion, of the groove 31, that extends in the axial direction is opposed to the through-hole 26*a* (see FIG. 4) of the first cylinder 11 shown in FIG. 4, in a state where the second cylinder 12 is inserted in the space 20 inside the first cylinder 11.

The groove 32 is composed of a portion that has a width in the up-down direction relative to the level of the height h1 from the lower end of the second cylinder 12, and that extends in the circumferential direction of the second cylinder 12. In a state where the second cylinder 12 is inserted in the space 20 inside the first cylinder 11, as shown in FIG. 10, the inner-side openings of the through-holes 22*a* to 22*j* of the first cylinder 11 are opposed to the portion, of the groove 32, that extends in the circumferential direction.

In a state where the valve body 13 is formed by combining the first cylinder 11 and the second cylinder 12 together, the grooves 31 and 32 formed in the second cylinder 12 are supplied with the resin A through any of the through-holes 21*a* to 21*j* and 22*a* to 22*j* provided in the first cylinder 11. Specifically, the groove 31 functions as a discharge path for the resin A and the groove 32 functions as a supply path for the resin A, which will be described later.

The groove 33 is composed of a portion that has a width in the up-down direction relative to the level of the height h2 from the lower end of the second cylinder 12, and that extends in the circumferential direction of the second cylinder 12. In a state where the second cylinder 12 is inserted in the space 20 inside the first cylinder 11, as shown in FIG. 10, the inner-side openings of the through-holes 23*a* to 23*j* of the first cylinder 11 are opposed to the portion, of the groove 33, that extends in the circumferential direction.

The groove 34 has: a portion that has a width in the up-down direction relative to the level of the height h2 from the lower end of the second cylinder 12, and that extends in the circumferential direction of the second cylinder 12; and a portion that extends in the axial direction of the second cylinder 12, and that reaches the position at the height h3 from the lower end of the second cylinder 12. In a state where the second cylinder 12 is inserted in the space 20 inside the first cylinder 11, as shown in FIG. 10, the inner-side openings of the through-holes 24*a* to 24*j* of the first cylinder 11 are opposed to the portion, of the groove 34, that extends in the circumferential direction. The lower end of the portion, of the groove 34, that extends in the axial direction is opposed to the through-hole 26*b* (see FIG. 4) of the first cylinder 11 shown in FIG. 4, in a state where the second cylinder 12 is inserted in the space 20 inside the first cylinder 11.

In a state where the valve body 13 is formed by combining the first cylinder 11 and the second cylinder 12 together, the grooves 33 and 34 formed in the second cylinder 12 are supplied with the resin B through any of the through-holes 23*a* to 23*j* and 24*a* to 24*j* provided in the first cylinder 11. Specifically, the groove 33 functions as a supply path for the resin B and the groove 34 functions as a discharge path for the resin B, which will be described later.

Figure 11:
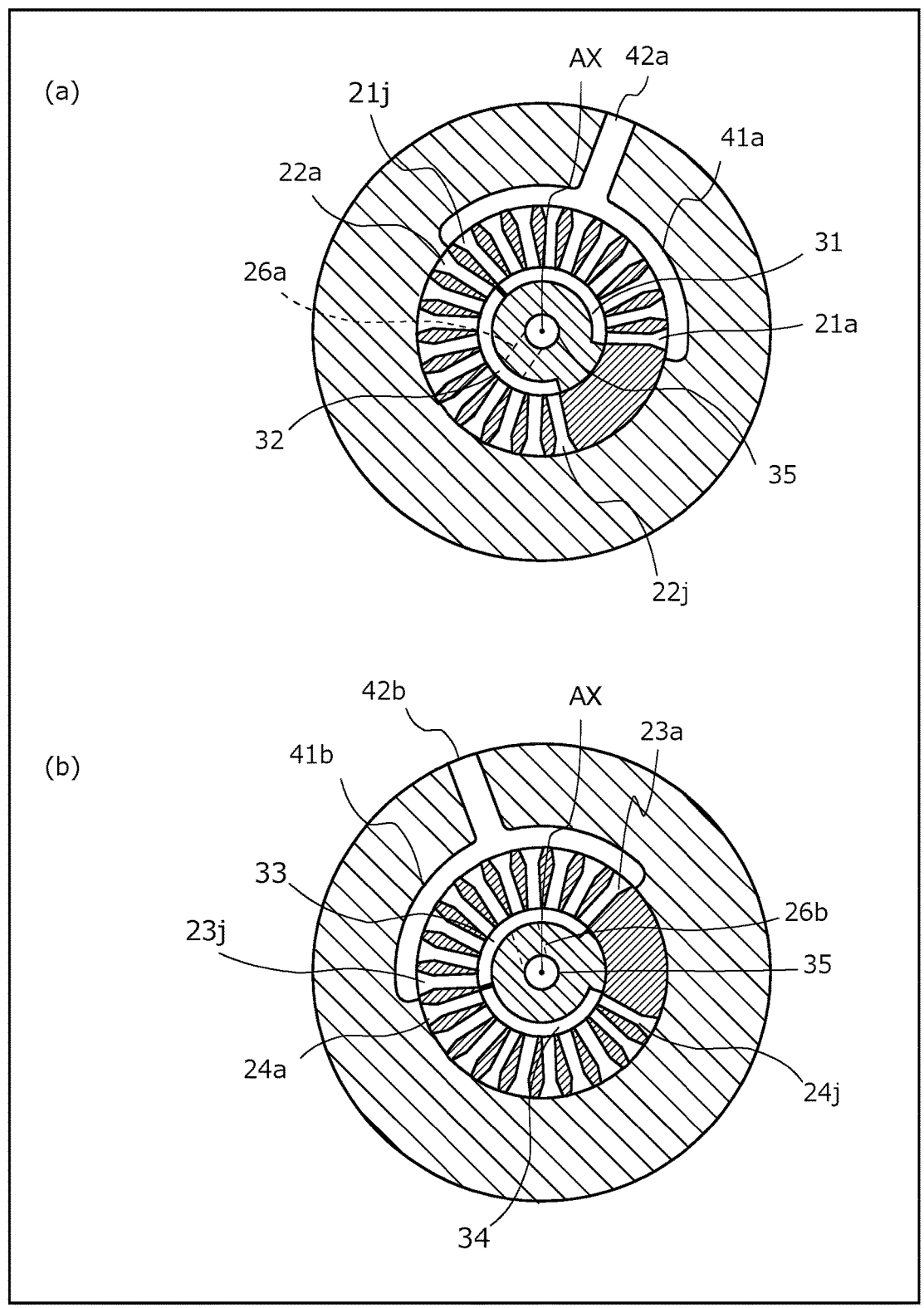
FIG. 11 is a cross-sectional view of a mixing valve according to a first embodiment.

FIG. 11 is cross-sectional views of a mixing valve according to an embodiment. More specifically, (a) of FIG. 11 corresponds to a cross-sectional view at a position along the line A-A shown in FIG. 3, and (b) of FIG. 11 corresponds to a cross-sectional view at a position along the line B-B shown in FIG. 3. For convenience in drawing, reference characters of the through-holes are omitted as appropriate. However, in (a) of FIG. 11, as in FIG. 5, the through-holes 21*a* to 21*j* and 22*a* to 22*j* are arranged in the counterclockwise direction about the axis AX, and in (b) of FIG. 11, as in FIG. 6, the through-holes 23*a* to 23*j* and 24*a* to 24*j* are arranged in the counterclockwise direction about the axis AX.

The mixing valve 4 shown in FIG. 11 is formed by inserting, into the accommodation space inside the valve case 14, the valve body 13 in which the second cylinder 12 is inserted in the first cylinder 11 with the relative rotation therebetween fixed. As described above, the accommodation space inside the valve case 14 is formed in a columnar shape that is substantially the same as the shape of the outer peripheral surface of the valve body 13 (the first cylinder 11). The valve body 13 is rotatable about the axis AX, with the outer peripheral surface of the valve body 13 sliding relative to the inner peripheral surface of the valve case 14.

At the time of assembling the valve body 13, as described with reference to FIG. 10, the rotational position of the second cylinder 12 relative to the first cylinder 11 is set (see FIGS. 4 to 10) such that: the inner-side openings of the through-holes 22*a* to 22*j* of the first cylinder 11 are opposed to the groove 32 of the second cylinder 12; the inner-side openings of the through-holes 23*a* to 23*j* of the first cylinder 11 are opposed to the groove 33 of the second cylinder 12; and further, the inner-side openings of the through-holes 24*a* to 24*j* of the first cylinder 11 are opposed to the groove 34 of the second cylinder 12. When the first cylinder 11 and the second cylinder 12 are positioned as above and fixed together, the flow paths as listed below are formed in the valve body 13.

Resin Supply Path for the Resin a to the Die:

Flow path extending from the through-holes 22*a* to 22*j* via the groove 32 and the flow-in path 36*a*, to the long hole 35.

Resin Discharge Path for the Resin A:

Flow path extending from the through-holes 21*a* to 21*j*, via the groove 31 and the through-hole 26*a*, to the discharge groove 25.

Resin Supply Path for the Resin B to the Die:

Flow path extending from the through-holes 23a to 23j, via the groove 33 and the flow-in path 36b, to the long hole 35.

Resin Discharge Path for the Resin B

Flow path extending from the through-holes 24a to 24j, via the groove 34 and the through-hole 26b, to the discharge groove 25.

Meanwhile, as shown in FIG. 11, supply paths 41a and 41b are formed in the valve case 14. The supply path 41a is composed of: a through-hole that has an opening 42a in the outer peripheral surface and that extends from this opening 42a to the inner peripheral surface; and a groove that is connected to this through-hole and that extends for a predetermined range, in the circumferential direction, of the inner peripheral surface. At least the groove portion of the supply path 41a is formed at a position where the groove portion of the supply path 41a can be opposed to the through-holes 21a to 21j and 22a to 22j of the first cylinder 11, in the axial direction of the first cylinder 11. Similarly, the supply path 41b is composed of: a through-hole that has an opening 42b in the outer peripheral surface and that extends from this opening 42b to the inner peripheral surface; and a groove that is connected to this through-hole and that extends for a predetermined range, in the circumferential direction, of the inner peripheral surface. At least the groove portion of the supply path 41b is formed at a position where the groove portion of the supply path 41b can be opposed to the through-holes 23a to 23j and 24a to 24j of the first cylinder 11, in the axial direction of the first cylinder 11. The opening 42a is supplied with the resin A from the first extruder, and the opening 42b is supplied with the resin B from the second extruder.

The lengths in the circumferential direction of the groove portions of the supply paths 41a and 41b provided in the inner peripheral surface of the valve case 14 are set such that the groove portions of the supply paths 41a and 41b can be each communicated with the same number of through-holes. In the present embodiment, the supply path 41a provided in the inner peripheral surface of the valve case 14 is set to have a length that allows the resin A to be supplied only to a half of the total number of the through-holes 21a to 21j and 22a to 22j (ten in the present embodiment). Similarly, the supply path 41b provided in the inner peripheral surface of the valve case 14 is set to have a length that allows the resin B to be supplied only to a half of the total number of the through-holes 23a to 23j and 24a to 24j (ten in the present embodiment). As shown in FIG. 11, the positional relationship in the rotation direction about the axis AX between each through-hole and the supply paths 41a and 41b is set such that the supply path 41b for the resin B is communicated with each of the through-holes 23a to 23j while the supply path 41a for the resin A is communicated with each of the through-holes 21a to 21j.

Although details are described later, when the valve body 13 is rotated about the axis AX, the positional relationship between the groove portion of the supply path 41a and the through-holes 21a to 21j and 22a to 22j is changed. As described above, the destination to which the through-holes 21a to 21j and 22a to 22j are connected are pre-determined. The through-holes 21a to 21j are connected to the resin discharge path and the through-holes 22a to 22j are connected to the resin supply path to the die. Therefore, when the positional relationship between the groove portion of the supply path 41a and the through-holes 21a to 21j and 22a to 22j is changed, the ratio between the number of the through-holes that are connected to the resin discharge path among the through-holes communicated with the supply path 41a, and the number of the through-holes that are connected to the resin supply path among the through-holes communicated with the supply path 41a is changed, although the number of through-holes communicated with the supply path 41a is unchanged. That is, by rotating the valve body 13, it is possible to vary the distribution ratio between the resin A to be discharged to the outside and the resin A to be supplied to the resin supply path to the die. In the present embodiment, the number of the through-holes to which the supply path 41a can supply the resin A at the same time, the number of the through-holes 21a to 21j connected to the resin discharge path, and the number of the through-holes 22a to 22j connected to the resin supply path are all 10. Therefore, the distribution ratio between the resin A to be discharged to the outside and the resin A to be supplied to the resin supply path to the die can be controlled at 11 levels within the range of 0:10 to 10:0.

In the present embodiment, the through-holes 23a to 23j and the through-holes 24a to 24j are also provided in the same valve body 13. Thus, when the valve body 13 is rotated about the axis AX, the positional relationship between the groove portion of the supply path 41b and the through-holes 23a to 23j and 24a to 24j is also changed. As described above, the through-holes 23a to 23j are connected to the resin supply path to the die, and the through-holes 24a to 24j are connected to the resin discharge path. Therefore, when the positional relationship between the groove portion of the supply path 41b and the through-holes 23a to 23j and 24a to 24j is changed, the ratio between the number of the through-holes that are connected to the resin supply path among the through-holes communicated with the supply path 41b, and the number of the through-holes that are connected to the resin discharge path among the through-holes communicated with the supply path 41b is changed, although the number of the through-holes communicated with the supply path 41b is unchanged. That is, by rotating the valve body 13, it is possible to vary the distribution ratio between the resin B to be supplied to the resin supply path to the die and the resin B to be discharged to the outside. In the present embodiment, the number of the through-holes to which the supply path 41b can supply the resin B at the same time, the number of the through-holes 23a to 23j connected to the resin supply path, and the number of the through-holes 24a to 24j connected to the resin discharge path are all 10. Therefore, the distribution ratio between the resin B to be supplied to the resin supply path to the die and the resin B to be discharged to the outside can be controlled at 11 levels within the range of 10:0 to 0:10, synchronized with the distribution of the resin A described above.

In the present embodiment, a first valve which distributes the resin A to the resin supply path and the resin discharge path is formed by: a portion of the valve body 13 in which the through-holes 21a to 21j and 22a to 22j are provided; and a portion of the valve case 14 in which the supply path 41a is provided. In addition, a second valve which distributes the resin B to the resin supply path and the resin discharge path is formed by: another portion of the valve body 13 in which the through-holes 23a to 23j and 24a to 24j are provided; and another portion of the valve case 14 in which the supply path 41b is provided. In a case where both the first valve and the second valve are formed by the same valve body 13 and the same valve case 14 in this manner, the distribution ratio in the first valve and the distribution ratio in the second valve can be changed in a synchronized manner, through rotation of the valve body 13 about a single axis AX. Thus, the mixing ratio of the resin A and the resin B can be easily controlled.

<Operation of Mixing Valve>

Figure 12:
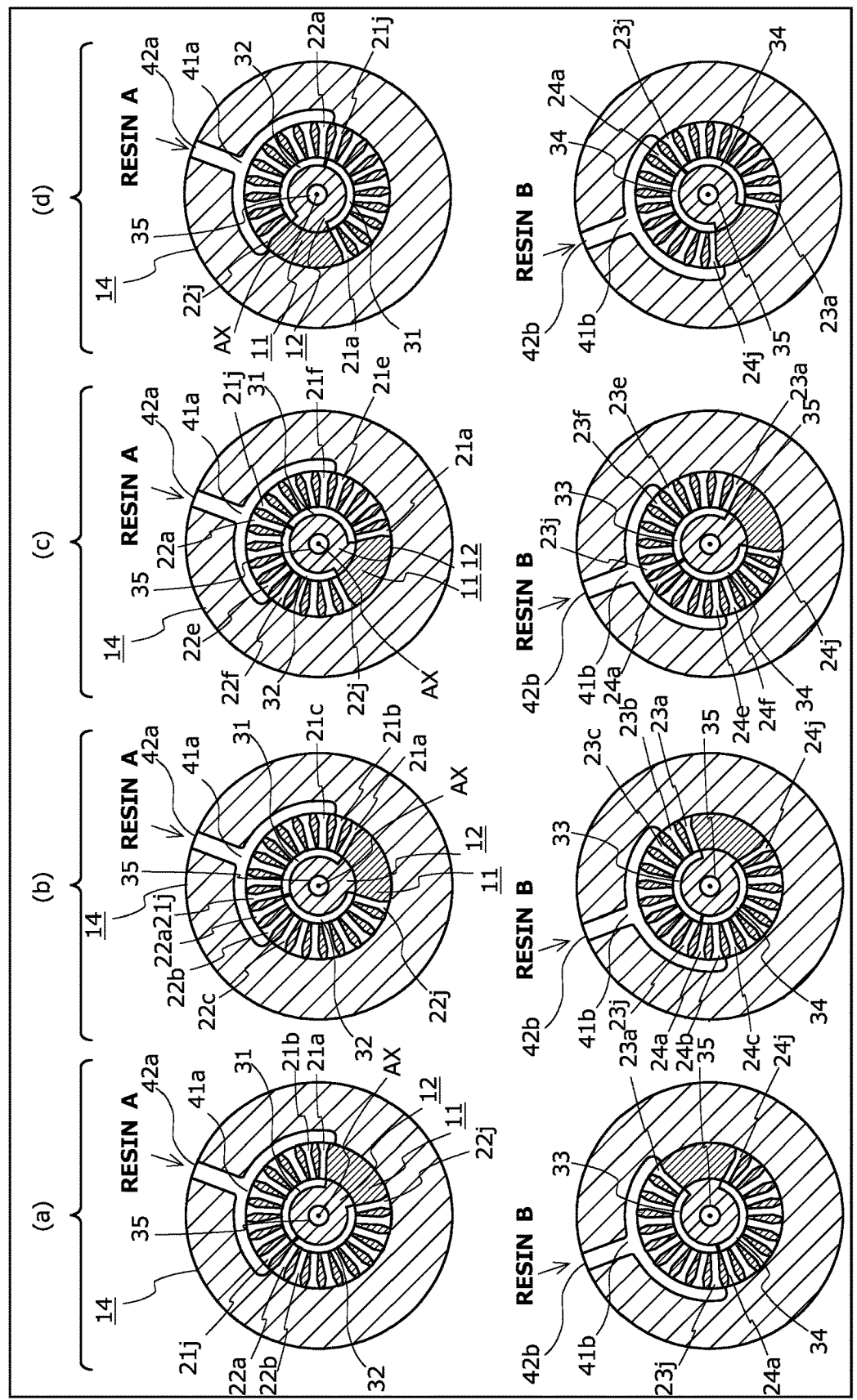
FIG. 12 is a diagram for describing a method for adjusting a resin mixing ratio by use of the mixing valve shown in FIG. 11.

FIG. 12 is diagrams for describing operation of the mixing valve shown in FIG. 11. Upper diagrams of (a) to (d) of FIG. 12 each show a cross section that corresponds to the position along the line A-A shown in FIG. 3, and lower diagrams of (a) to (d) of FIG. 12 each show a cross section that corresponds to the position along the line B-B shown in FIG. 3. For convenience in drawing, reference characters of the through-holes are omitted as appropriate. However, in the upper diagrams of (a) to (d) of FIG. 12, as in FIG. 5, the through-holes 21a to 21j and 22a to 22j are arranged in the counterclockwise direction about the axis AX, and in the lower diagrams of (a) to (d) of FIG. 12, as in FIG. 6, the through-holes 23a to 23j and 24a to 24j are arranged in the counterclockwise direction about the axis AX. In FIG. 12, portions having the same hatching pattern represent the same members, and reference characters thereof are not indicated as appropriate.

(State a)

First, the upper diagram of (a) of FIG. 12 shows a state in which the supply path 41a for the resin A is communicated with all of the through-holes 21a to 21j of the first cylinder 11. In this state, the resin A supplied from the first extruder through the opening 42a flows from the through-holes 21a to 21j of the first cylinder 11 into the groove 31 of the second cylinder 12, passes through the through-hole 26a and the discharge groove 25 (see FIG. 4) of the first cylinder 11, and is discharged to the outside of the mixing valve 4, and thus, is not supplied to the die.

In this state, as shown in the lower diagram of (a) of FIG. 12, the supply path 41b for the resin B is communicated with all of the through-holes 23a to 23j of the first cylinder 11. Therefore, all of the resin B supplied from the second extruder 3b through the opening 42b flows from the through-holes 23a to 23j of the first cylinder 11 into the groove 33 of the second cylinder 12, passes through the flow-in path 36b and the long hole 35 (see FIGS. 8 to 10) of the second cylinder 12, and is supplied to the die.

That is, when the valve body 13 is at the rotational position shown in (a) of FIG. 12, the resin A is all discharged, and the resin B is all supplied to the die. Thus, the mixing ratio between the resin A and the resin B is 0:10.

(State b)

Next, the upper diagram of (b) of FIG. 12 shows a state realized when the valve body 13 is rotated about the axis AX in the clockwise direction in FIG. 12 by an angle that corresponds to two through-holes, from the state shown in (a) of FIG. 12. As described above, the supply path 41a has a length that allows the supply path 41a to be communicated with ten through-holes that are consecutive in the circumferential direction. Therefore, when the valve body 13 is rotated by an angle that corresponds to two through-holes, communication between the two through-holes 21a and 21b at the most clockwise side and the supply path 41a is canceled, and the eight through-holes 21c to 21j of the first cylinder 11 and the two through-holes 22a and 22b consecutive thereto are communicated with the supply path 41a for the resin A.

In this state, of the resin A supplied from the first extruder 3a through the opening 42a, a portion that has been supplied to the through-holes 21c to 21j of the first cylinder 11 (8/10 of the supplied resin A) flows into the groove 31 of the second cylinder 12, and then, is discharged to the outside of the mixing valve 4. However, the other portion of the resin A that has been supplied to the through-holes 22a and 22b (2/10 of the supplied resin A) flows into the groove 32 of the second cylinder 12, passes through the flow-in path 36a, and flows into the long hole 35.

At this time, the rotational position between the supply path 41b for the resin B and the valve body 13 is also shifted by the angle corresponding to two through-holes. Thus, as shown in the lower diagram of (b) of FIG. 12, the supply path 41b for the resin B is communicated with the eight through-holes 23c to 23j of the first cylinder 11 and with the two through-holes 24a and 24b consecutive thereto. Of the resin B supplied from the second extruder 3b through the opening 42b, a portion that has been supplied to the through-holes 23c to 23j of the first cylinder 11 (8/10 of the supplied resin B) flows from the through-holes 23c to 23j of the first cylinder 11 into the groove 33 of the second cylinder 12, passes through the flow-in path 36b of the second cylinder, and is supplied to the long hole 35. Of the resin B supplied from the opening 42b, the other portion that has been supplied to the through-holes 24a and 24b of the first cylinder 11 (2/10 of the supplied resin B) flows into the groove 34 of the second cylinder 12, passes through the through-hole 26b and the discharge groove 25 of the first cylinder 11, and is discharged to the outside of the mixing valve 4.

That is, when the valve body 13 is at the rotational position shown in (b) of FIG. 12, the resin A having been supplied to two of the ten through-holes communicated with the supply path 41a and the resin B having been supplied to eight of the ten through-holes communicated with the supply path 41b are supplied to the long hole 35 of the second cylinder 12, and are mixed together in the long hole 35 to be supplied to the die. The other of the resins that have been supplied is discharged to the outside. Thus, when the valve body 13 is at the rotational position shown in (b) of FIG. 12, the mixing ratio between the resin A and the resin B is 2:8.

(State c)

Next, the upper diagram of (c) of FIG. 12 shows a state realized when the valve body 13 is rotated about the axis AX in the clockwise direction in FIG. 12 by an angle that corresponds to three through-holes, from the state shown in (b) of FIG. 12. As described above, the supply path 41a has a length that allows the supply path 41a to be communicated with ten through-holes that are consecutive in the circumferential direction. Therefore, when the valve body 13 is rotated by an angle that corresponds to three through-holes, communication between the three through-holes 21c to 21e and the supply path 41a is canceled, and the five through-holes 21f to 21j of the first cylinder 11 and the five through-holes 22a to 22e consecutive thereto are communicated with the supply path 41a for the resin A.

In this state, of the resin A supplied from the first extruder 3a through the opening 42a, a portion that has been supplied to the through-holes 21f to 21j of the first cylinder 11 (5/10 of the supplied resin A) flows into the groove 31 of the second cylinder 12, and then is discharged to the outside of the mixing valve 4. However, the other portion of the resin A that has been supplied to the through-holes 22a to 22e (5/10 of the supplied resin A) flows into the groove 32 of the second cylinder 12, passes through the flow-in path 36a, and flows into the long hole 35.

At this time, the rotational position between the supply path 41b for the resin B and the valve body 13 is also shifted by the angle corresponding to three through-holes. Thus, in a state where the supply path 41a for the resin A is communicated with the through-holes 21f to 21j of the first cylinder 11 and with the five through-holes 22a to 22e consecutive thereto, the supply path 41b for the resin B is communicated with the five through-holes 23f to 23j of the first cylinder 11 and with the five through-holes 24a to 24e consecutive thereto, as shown in the lower diagram of (c) of FIG. 12. Of the resin B supplied from the second extruder 3b through the opening 42b, a portion that has been supplied to the through-holes 23f to 23j of the first cylinder 11 (5/10 of the supplied resin B) flows from the through-holes 23f to 23j of the first cylinder 11 into the groove 33 of the second cylinder 12, passes through the flow-in path 36b of the second cylinder, and is supplied to the long hole 35. Of the resin B supplied from the opening 42b, the other portion that has been supplied to the through-holes 24a to 24e of the first cylinder 11 (5/10 of the supplied resin B) flows into the groove 34 of the second cylinder 12, passes through the through-hole 26b and the discharge groove 25 of the first cylinder 11, and is discharged to the outside of the mixing valve 4.

That is, when the valve body 13 is at the rotational position shown in (c) of FIG. 12, the resin A having been supplied to five of the ten through-holes communicated with the supply path 41a, and the resin B having been supplied to five of the ten through-holes communicated with the supply path 41b are supplied to the long hole 35 of the second cylinder 12, and are mixed together in the long hole 35 to be supplied to the die. The other of the resins that have been supplied is discharged. Thus, when the valve body 13 is at the rotational position shown in (c) of FIG. 12, the mixing ratio between the resin A and the resin B is 5:5.

(State d)

Next, the upper diagram of (d) of FIG. 12 shows a state realized when the valve body 13 is rotated about the axis AX in the clockwise direction in FIG. 12 by an angle that corresponds to five through-holes, from the state shown in (c) of FIG. 12. As described above, the supply path 41a has a length that allows the supply path 41a to be communicated with ten through-holes that are consecutive in the circumferential direction. Therefore, when the valve body 13 is rotated by an angle that corresponds to five through-holes, communication between the through-holes 21f to 21j and the supply path 41a is canceled, and all of the ten through-holes 22a to 22j at the most counterclockwise side are communicated with the supply path 41a for the resin A. In this state, the resin A supplied from the first extruder 3a through the opening 42a flows from the through-holes 22a to 22j of the first cylinder 11 into the groove 32 of the second cylinder 12, passes through the flow-in path 36a of the second cylinder 12, and flows into the long hole 35.

In this state, as shown in the lower diagram of (d) of FIG. 12, the supply path 41b for the resin B is communicated with all of the through-holes 24a to 24j of the first cylinder 11. Therefore, all of the resin B supplied from the second extruder 3b through the opening 42b flows from the through-holes 24a to 24j of the first cylinder 11 into the groove 34 of the second cylinder 12, passes through the through-hole 26b and the discharge groove 25 of the first cylinder 11, and is discharged to the outside of the mixing valve 4.

Thus, when the valve body 13 is at the rotational position shown in (d) of FIG. 12, the resin A is all supplied to the die, and the resin B is all discharged. Thus, the mixing ratio between the resin A and the resin B is 10:0.

With respect to FIG. 12, examples in which the mixing ratios between the resin A and the resin B are respectively 0:10, 2:8, 5:5, and 10:0 have been described. However, the resin A and the resin B can also be mixed at a mixing ratio between 0:10 to 10:0, depending on the rotational position of the valve body 13. In addition, the mixing ratio can be adjusted in a desired range by increasing or decreasing the number of through-holes.

As described above, in the catheter shaft production apparatus 100 according to the present embodiment, the ratio between: a number "a" of through-holes that are communicated with the resin discharge path among the through-holes communicated with the supply path 41a for the resin A; and a number "b" of through-holes that are communicated with the resin supply path (the long hole 35) for supplying resin to the die among the through-holes communicated with the supply path 41a for the resin A, is equal to the ratio between: a number "c" of through-holes that are communicated with the resin supply path (the long hole 35) for supplying resin to the die among the through-holes communicated with the supply path 41b for the resin B; and a number "d" of through-holes that are communicated with the resin discharge path among the through-holes communicated with the supply path 41b for the resin B (where a, b, c, and d are each an integer not smaller than 0). In other words, irrespective of the rotation angle of the valve body 13, the number of through-holes being used for supplying the resin A always matches the number of through-holes being used for discharging the resin B, and the number of through-holes being used for discharging the resin A always matches the number of through-holes being used for supplying the resin B. In addition, the number of through-holes communicated with the supply path 41a for the resin A is equal to the number of through-holes communicated with the supply path 41b for the resin B. Thus, the number of through-holes communicated with the resin supply path (the long hole 35) (i.e., the sum of the number "b" of through-holes and the number "c" of through-holes described above) is constant.

With this configuration, when the distribution ratios of the resin A and the resin B are changed according to the rotation angle of the valve body 13, the supply mount of the resin B decreases by the amount that corresponds to increase in the supply mount of the resin A to the long hole 35. Thus, the mixing proportion between the resin A and the resin B can be adjusted. In a very short period before and after the valve body 13 is rotated, the mixing proportion between the resin A and the resin B supplied to the long hole 35 sharply changes (in the case of the present embodiment, rotation of the valve body 13 corresponding to one through-hole causes 10% change in the mixing proportion). However, the resin before the mixing proportion is changed remains in the flow path of the resin extending from the long hole 35 to the extrusion hole of the die, and the resin is supplied to the die together with this remaining resin. Therefore, the mixing proportion of the resin extruded from the extrusion hole of the die changes not sharply but gradually. If an outer layer tube of the catheter shaft is extrusion-molded while the valve body 13 is rotated, the mixing proportion between the resin A and the resin B forming the outer layer tube can be continuously varied, in association with the molding of the catheter shaft. If resins having different hardnesses are used as the resin A and the resin B, the hardness of the outer layer tube can be gradually increased or decreased across one end side to the other end side of the catheter shaft. Therefore, with the catheter shaft production apparatus 100 according to the present embodiment, compared with conventional production methods, a catheter shaft whose hardness is naturally varied along the length direction thereof can be produced.

As a method for varying the resin mixing proportion, a method is conceivable in which the rotation speeds of the screws or gear pumps of the first extruder and the second extruder are varied to adjust the ejection amount (volume) per unit time. However, even if the rotation speeds of the screws or the gear pumps are changed, since the resin is present in the flow path and the die, the pressure (internal pressure) of the resin does not change instantly. This results in poor responsiveness of the resin extrusion speed to the change in the rotation speeds of the screws or the gear pumps, which causes difficulty in accurate control of the resin mixing ratio and of the ejection amount from the die. Therefore, if the resin mixing ratio is controlled by adjusting the extrusion speeds of the first extruder and the second extruder respectively, there is a problem that the accuracy in terms of the change rate of the hardness and in terms of the outer diameter dimension of the molded outer layer tube is reduced. In particular, in a catheter whose outer diameter is about 0.5 to 1.8 mm as in a blood vessel catheter, if the hardness and the outer diameter thereof are varied from design values, insertion of the catheter into a blood vessel becomes difficult in some cases. In contrast to this, in the catheter shaft production apparatus 100 according to the present embodiment, the mixing ratio between the resin A and the resin B is adjusted by changing the distribution ratios (the ratio between supply mount and discharge amount) of the resin A and the resin B, and thus, there is no need to change the extrusion amounts of the first extruder and the second extruder. Therefore, even when the distribution ratios of the resin A and the resin B in the mixing valve are changed, the extrusion amounts of the resin A and the resin B to be supplied to the die are not changed and are kept constant. Therefore, variation in the volume of the resin to be extruded from the outlet can be suppressed, and the mixing ratio between the resin A and the resin B can be controlled in good responsiveness. Thus, the hardness and the outer diameter of the molded catheter shaft can be kept constant with high accuracy.

Second Embodiment

Figure 13:
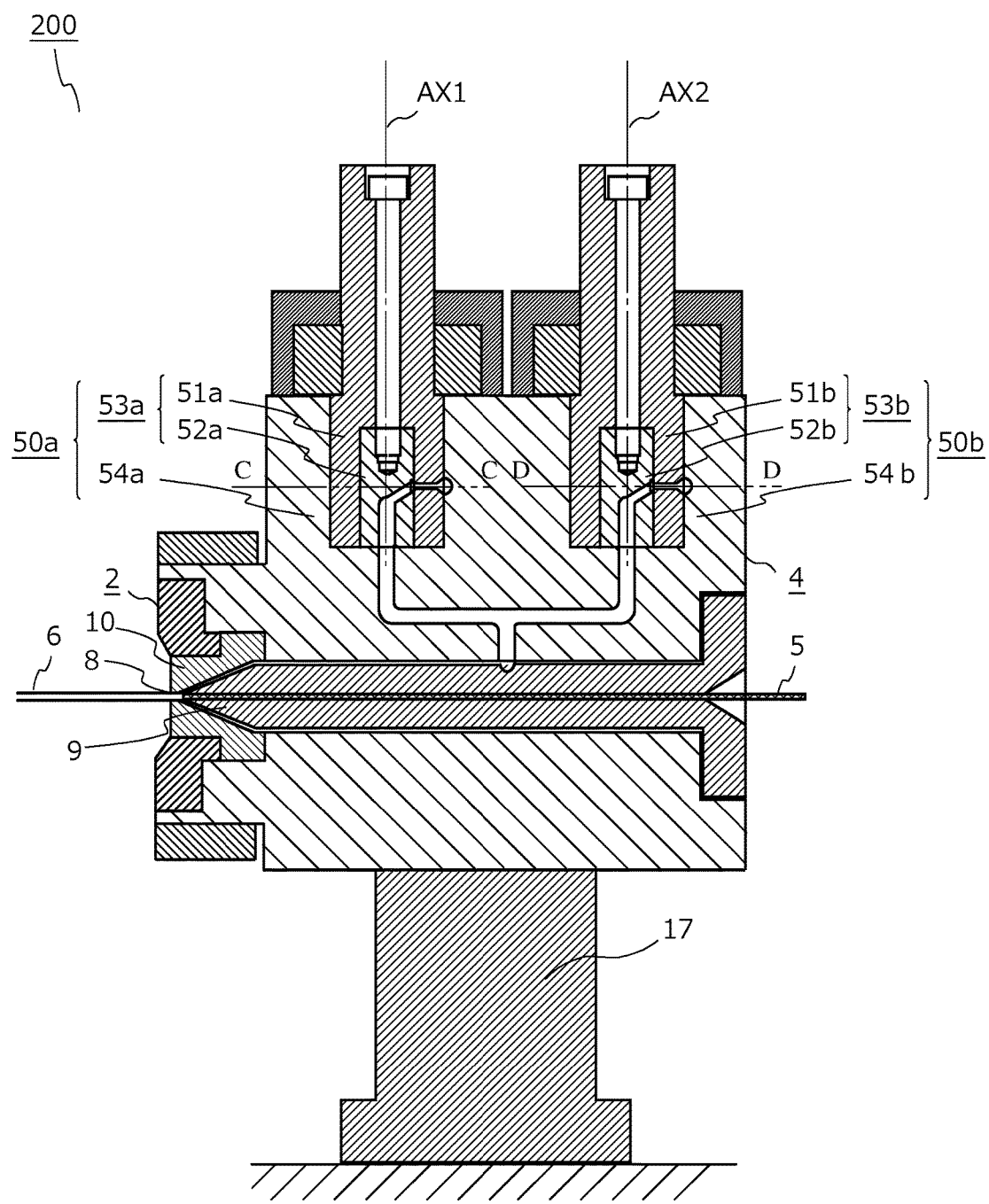
FIG. 13 is a cross-sectional view of a catheter shaft production apparatus according to a second embodiment.

FIG. 13 is a front view of a catheter shaft production apparatus according to a second embodiment.

In the first embodiment described above, the first valve and the second valve are formed in an integrated manner in a single valve body 13 and a single valve case 14. However, in the second embodiment, the first valve and the second valve are formed as separate bodies. Hereinafter, the difference between the present embodiment and the first embodiment is mainly described.

A catheter shaft production apparatus 200 according to the present embodiment includes: the die 2; a first extruder and a second extruder which are not shown; and the mixing valve 4, as shown in FIG. 13. The catheter shaft production apparatus 200 according to the present embodiment is also fixed to a predetermined mounting base or the like with the pedestal 17 interposed therebetween. Although not shown, a supply device for supplying the blade wire 5 to the catheter shaft production apparatus 200, a haul-off device for hauling off a catheter shaft having been extrusion-molded, and the like are provided as appropriate.

The mixing valve 4 according to the present embodiment is composed of a first valve 50a and a second valve 50b which are formed as separate bodies.

The first valve 50a is composed of a valve body 53a and a valve case 54a. The valve body 53a composed of: a hollow first cylinder 51a; a second cylinder 52a housed in the first cylinder 51a; and a shaft body which fixes the first cylinder 51a and the second cylinder 52a together. A space having a columnar shape that is substantially the same as an outer shape of the valve body 53a is provided in the valve case 54a. The valve body 53a is accommodated in this space. In a state where the valve body 53a is housed in the valve case 54a, the valve body 53a is rotatable about an axis AX1, with the outer peripheral surface of the valve body 53a sliding relative to the inner peripheral surface of the valve case 54a.

The first cylinder 51a and the second cylinder 52a are configured substantially the same as the first cylinder 11 and the second cylinder 12 according to the first embodiment. Specifically, the first cylinder 51a is provided with the through-holes 21a to 21j and the through-holes 22a to 22j similarly to the first cylinder 11 shown in FIGS. 4 to 7, but is not provided with the through-holes 23a to 23j and the through-holes 24a to 24j. The second cylinder 52a is provided with the grooves 31 and 32 and the flow-in path 36a similarly to the second cylinder 12 shown in FIG. 8, but is not provided with the grooves 33 and 34 and the flow-in path 36b.

The valve case 54a is configured substantially the same as the valve case 14 according to the first embodiment. Specifically, similarly to the valve case 14 shown in FIG. 11, the valve case 54a has a supply path formed therein that supplies the resin A ejected from the first extruder, to a half of the numbers of the through-holes 21a to 21j and 22a to 22j provided in the first cylinder 51a. The shape and the dimensions of this supply path are the same as those of the supply path 41a described in the first embodiment. The cross section along the line C-C shown in FIG. 13 is the same as the cross section shown in (a) of FIG. 11.

The second valve 50b is composed of a valve body 53b and a valve case 54b. The valve body 53b is composed of: a hollow first cylinder 51b; a second cylinder 52b housed in the first cylinder 51b; and a shaft body which fixes the first cylinder 51b and the second cylinder 52b together. A space having a columnar shape that is substantially the same as an outer shape of the valve body 53b is provided in the valve case 54b. The valve body 53b is accommodated in this space. In a state where the valve body 53b is housed in the valve case 54b, the valve body 53b is rotatable about an axis AX2, with the outer peripheral surface of the valve body 53b sliding relative to the inner peripheral surface of the valve case 54b.

The first cylinder 51b and the second cylinder 52b are configured similarly to the first cylinder 51a and the second cylinder 52b described above. In addition, the valve case 54b is also configured similarly to the valve case 54a described above. The valve case 54b has a supply path formed therein that supplies the resin B ejected from the second extruder, to a half of the number of the through-holes provided in the first cylinder 51b. The cross section along the line D-D shown in FIG. 13 is the same as the cross section shown in (b) of FIG. 11.

A drive mechanism such as an actuator is provided above each of the valve cases 54a and 54b. The drive mechanisms rotate the valve body 53a about the axis AX1 and the valve body 53b about the axis AX2, respectively, in accordance with control of a control device not shown. In the present embodiment, the valve cases 54a and 54b are integrated together, but may be provided as separate bodies, respectively.

Here, a method for changing the mixing proportion between the resin A and the resin B by use of the first valve 50a and the second valve 50b is described. Also in the present embodiment, as in the first embodiment, the mixing proportion between the resin A and the resin B is varied, by changing the distribution ratio of the resin A in the first valve 50a and the distribution ratio of the resin B in the second valve 50b without changing the extrusion amounts from the first extruder and the second extruder. However, in the present embodiment, since the first valve 50a and the second valve 50b are provided as separate bodies, the valve bodies 53a and 53b are rotated so as to be synchronized with each other such that: the number of through-holes being used for supplying the resin A always matches the number of through-holes being used for discharging the resin B; the number of through-holes being used for discharging the resin A always matches the number of through-holes being used for supplying the resin B; and the number of through-holes communicated with the resin supply path (the long hole 35) (i.e., the sum of the number "b" of through-holes and the number "c" of through-holes described above) is constant.

The resin A having been supplied from the first valve 50a toward the die 2 and the resin B having been supplied from the second valve 50b toward the die are mixed together in a flow path connected to the die 2, and the resultant resin flows in the resin flow path between the inner mold 9 and the outer mold 10 of the die 2, to be extruded onto the surface of the blade wire 5 in the extrusion hole 8, whereby the catheter shaft 6 is molded.

Also in the catheter shaft production apparatus 200 according to the present embodiment, if the distribution ratios of the resin A and the resin B are changed according to the rotation angle of the valve bodies 53a and 53b, and the supply mount of the resin B is decreased by an amount that corresponds to increase in the supply mount of the resin A to the resin supply path, the mixing proportion between the resin A and the resin B forming the outer layer tube can be continuously varied while the volume of the resin extruded per unit time from the extrusion hole 8 of the die 2 is kept constant. If resins having different hardnesses are used as the resin A and the resin B, the hardness of the outer layer tube can be gradually increased or decreased from one end side to the other end side of the catheter shaft. Thus, with the catheter shaft production apparatus 200 according to the present embodiment, compared with conventional production methods, a catheter shaft whose hardness is naturally varied along the length direction can be produced.

In a case where two valves are provided independently of each other as in the present embodiment, and if the viscosities, the flowabilities, or the like of the resin A and the resin B are greatly different from each other, the designs of the first valve and the second valve can be changed in accordance with the properties of the resins.

Modification of the Second Embodiment

Since the catheter shaft production apparatus 200 according to the second embodiment described above can control the resin distribution ratios in the first valve 50a and the second valve 50b independently of each other, it is also possible to increase or decrease the total of the supply mount of the resin A to the resin supply path and the supply mount of the resin B to the resin supply path. Specifically, in the first and second embodiments described above, when the distribution proportions of the resin A and the resin B are to be changed, the increased amount of one resin is caused to match the decreased amount of the other resin, so that the total resin supply mount is kept constant. However, if the increased amount of one resin is intentionally caused to be different from the decreased amount of the other resin, an outer layer tube having a tapered shape can be formed.

In general, a catheter shaft having an outer layer tube in a tapered shape can be formed by increasing or decreasing the haul-off speed of the haul-off device while keeping constant the volume of the resin extruded from the extrusion hole of the die per unit time. However, the taper angle of a taper formed by adjusting the haul-off speed has limitation.

In contrast to this, as in the present modification, if the distribution ratio of the resin A in the first valve and the distribution ratio of the resin B in the second valve are changed while the total of the supply mount of the resin A from the first valve 50a to the resin supply path and the supply mount of the resin B from the second valve 50b to the resin supply path are increased or decreased, the mixing proportion between a first resin and a second resin can be increased or decreased while the outer diameter of the outer layer tube is increased or decreased in association with molding of the catheter shaft. With the catheter shaft production apparatus according to the present modification, it is possible to change the resin mixing proportion, while providing the outer layer tube with a taper. For example, by use of resins having different hardnesses as two kinds of resins, it is possible to produce a catheter shaft in which the leading end portion thereof is thin and soft, the outer diameter thereof is gradually increased toward the proximal end side thereof, and the proximal end side portion is thick and rigid.

Third Embodiment

Figure 14:
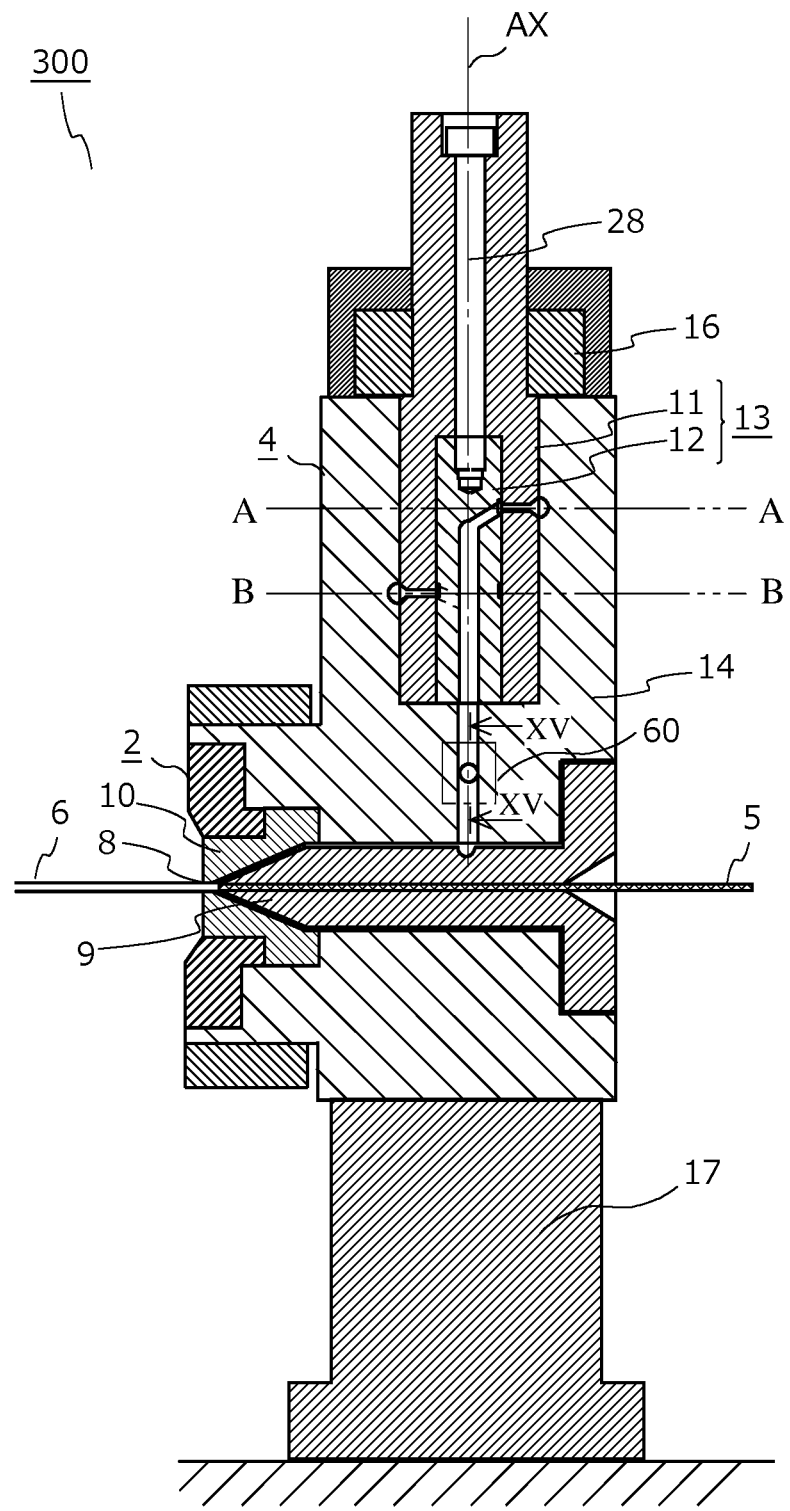
FIG. 14 is a cross-sectional view of a catheter shaft production apparatus according to a third embodiment.
Figure 15:
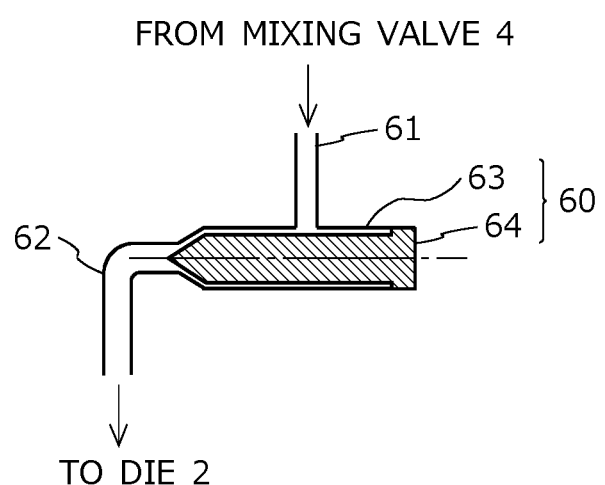
FIG. 15 is a cross-sectional view taken along a line XV-XV shown in FIG. 14.

FIG. 14 is a cross-sectional view of a catheter shaft production apparatus according to a third embodiment, and FIG. 15 is a cross-sectional view taken along the line XV-XV shown in FIG. 14.

A catheter shaft production apparatus 300 according to the third embodiment is obtained by further providing a resin mixing portion 60 to the catheter shaft production apparatus 100 according to the first embodiment shown in FIG. 1. Since configurations of the catheter shaft production apparatus 300 other than the resin mixing portion 60 are the same as those of the catheter shaft production apparatus 100 according to the first embodiment, repeated description thereof is omitted.

The resin mixing portion 60 is provided in a resin flow path extending from the junction for the resin A and the resin B to the die 2, and is a mechanism that actively mixes the resin A and the resin B together. In the present embodiment, as shown in FIG. 15, the resin mixing portion 60 is composed of: a mixing barrel 63 provided between a flow path 61 connected to the mixing valve 4 and a flow path 62 connected to the die 2; and a mixing screw 64 inserted in the mixing barrel 63. The mixing screw 64 is connected to a drive mechanism not shown. When the mixing screw 64 is rotated about the central axis thereof by the drive mechanism, the mixing screw 64 mixes the resin A and the resin B supplied to the mixing barrel 63 through the flow path 61 from the mixing valve 4, and extrudes the mixed resin to the die 2 through the flow path 62. Here, an example has been described in which the resin mixing portion 60 is formed by a uniaxial mixing screw 64. However, the configuration of the resin mixing portion 60 is not limited in particular as long as the resin mixing portion 60 can mix two kinds of resins, i.e., the resin A and the resin B, supplied from the mixing valve 4. The resin mixing portion 60 may be formed by a biaxial screw extruder such as a kneading disc.

In the catheter shaft production apparatus 300 according to the third embodiment, two kinds of resins, i.e., the resin A and the resin B, are actively mixed in the resin mixing portion 60, and thus, the resin A and the resin B can be more uniformly mixed and uneven mixture thereof can be hindered. Therefore, with the catheter shaft production apparatus 300 according to the present embodiment, since uneven mixture of two kinds of resins, i.e., the resin A and the resin B, is hindered, the hardness of the resin can be made more smoothly varied in the length direction of the catheter shaft. Depending on the kind or the grade of the resin A and the resin B that are used, there may be cases where the resin A and the resin B are difficult to be mixed together. However, with the catheter shaft production apparatus 300 according to the present embodiment, even in a case of a combination of two kinds of resins, i.e., the resin A and the resin B, that are difficult to be mixed together, the resins can be mixed uniformly.

Fourth Embodiment

Figure 16:
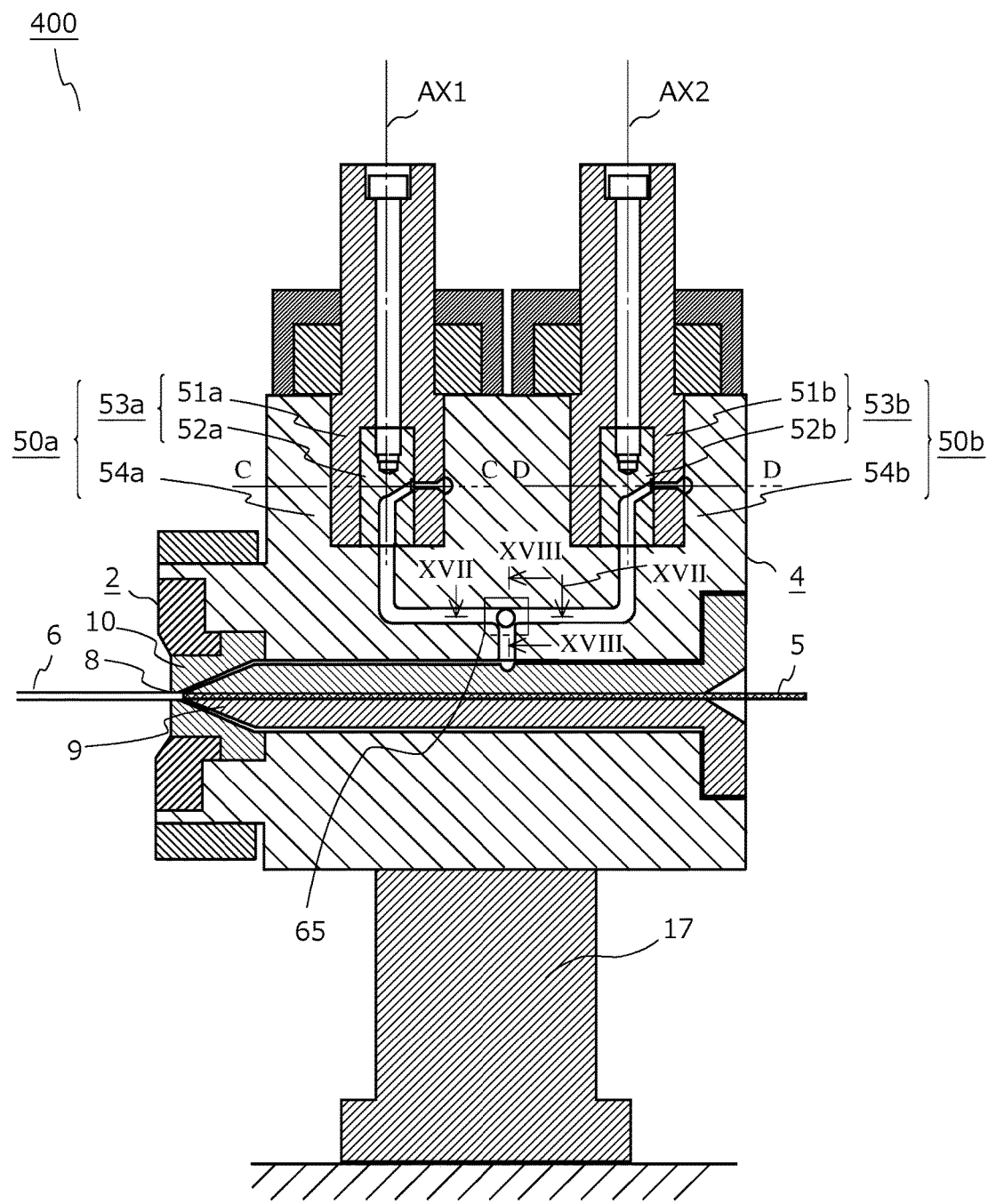
FIG. 16 is a cross-sectional view of a catheter shaft production apparatus according to a fourth embodiment.
Figure 17:
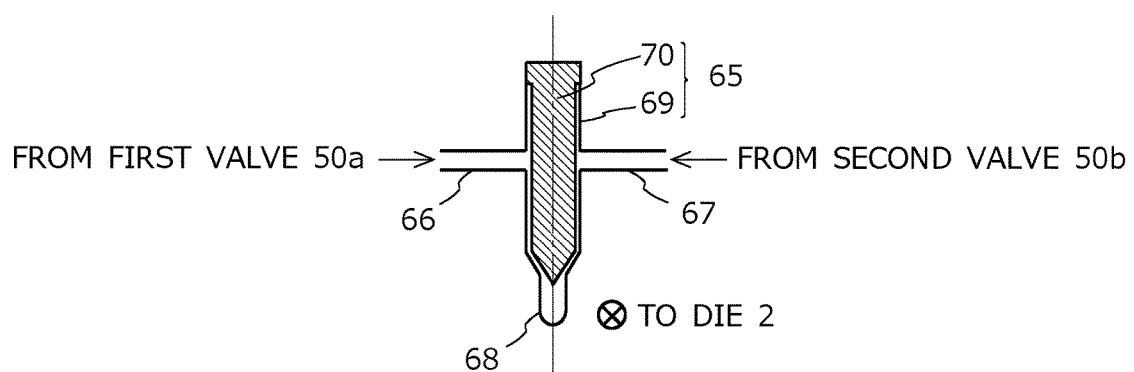
FIG. 17 is a cross-sectional view taken along a line XVII-XVII shown in FIG. 16.
Figure 18:
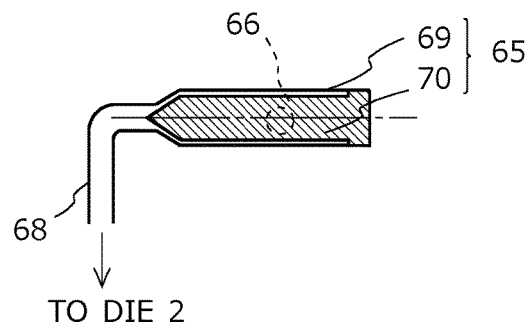
FIG. 18 is a cross-sectional view taken along a line XVIII-XVIII shown in FIG. 16.
Figure 19:
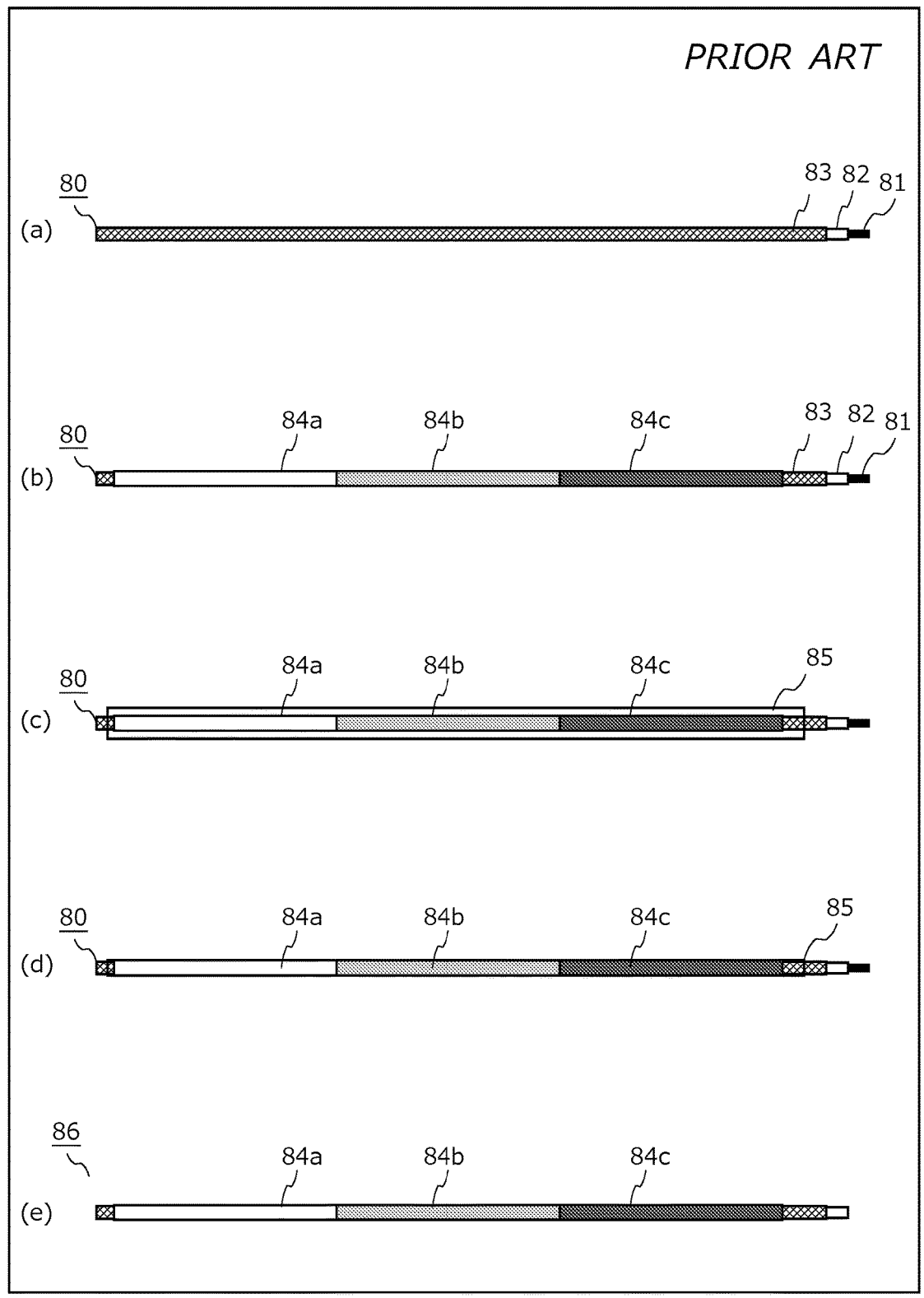
FIG. 19 is a schematic drawing of processes showing a general production method for producing a catheter shaft whose hardness is varied stepwise along the length direction thereof.

FIG. 16 is a cross-sectional view of a catheter shaft production apparatus according to a fourth embodiment, FIG. 17 is a cross-sectional view taken along the line XVII-XVII shown in FIG. 16, and FIG. 18 is a cross-sectional view taken along the line XVIII-XVIII shown in FIG. 16.

A catheter shaft production apparatus 400 according to the fourth embodiment is obtained by further providing a resin mixing portion 65 to the catheter shaft production apparatus 200 according to the second embodiment shown in FIG. 13. Since configurations of the catheter shaft production apparatus 400 other than the resin mixing portion 65 are the same as those of the catheter shaft production apparatus 100 according to the second embodiment, repeated description thereof is omitted.

The resin mixing portion 65 is provided at the junction for the resin A and the resin B, and is a mechanism that actively mixes the resin A and the resin B together. In the present embodiment, as shown in FIGS. 17 and 18, the resin mixing portion 65 is composed of: a mixing barrel 69 provided between a flow path 68 connected to the die 2, and a junction of a flow path 66 connected to the first valve 50a and a flow path 67 connected to the second valve 50b; and a mixing screw 70 inserted in the mixing barrel 69. The mixing screw 70 is connected to a drive mechanism not shown. When the mixing screw 70 is rotated about the central axis thereof by the drive mechanism, the mixing screw 70 mixes the resin A and the resin B supplied to the mixing barrel 69 through the flow paths 66 and 67, and extrudes the mixed resin to the die 2 through the flow path 68. Here, an example has been described in which the resin mixing portion 65 is formed by a uniaxial mixing screw 70. However, the configuration of the resin mixing portion 65 is not limited in particular as long as the resin mixing portion 65 can mix two kinds of resins supplied, i.e., the resin A and the resin B. The resin mixing portion 65 may be formed by a biaxial screw extruder such as a kneading disc.

In the catheter shaft production apparatus 400 according to the fourth embodiment, two kinds of resins, i.e., the resin A and the resin B, are actively mixed in the resin mixing portion 65, and thus, the resin A and the resin B can be more uniformly mixed and uneven mixture thereof can be hindered. Therefore, with the catheter shaft production apparatus 400 according to the present embodiment, since uneven mixture of two kinds of resins, i.e., the resin A and the resin B, is hindered, the hardness of the resin can be made more smoothly varied in the length direction of the catheter shaft. Depending on the kind and the grade of the resin A and the resin B that are used, there may be cases where the resin A and the resin B are difficult to be mixed together. However, with the catheter shaft production apparatus 400 according to the present embodiment, even in a case of a combination of two kinds of resins, i.e., the resin A and the resin B, that are difficult to be mixed together, the resin can be mixed uniformly.

(Other Modifications)

In each embodiment described above, an example has been described in which the present invention is applied to a catheter shaft production apparatus. However, the configurations of the mixing valve and the production apparatus according to the present invention can be applied to a production apparatus for a flexible tube having another usage such as a tube for an endoscope.

In each embodiment described above, an example has been described in which a catheter shaft is extrusion-molded by use of resins having different hardnesses as two different kinds of resins. However, as the two kinds of resins, resins that are different in any properties, not limited to hardness, may be used. For example, if resins having different colors are used as the two kinds of resins, it is also possible to produce an outer layer tube whose color gradually changes from the leading end thereof toward the proximal end side thereof.

In each embodiment described above, the valve case may be divided into a plurality of blocks as appropriate so as to facilitate formation of grooves and flow paths.

In each embodiment described above, an example has been described in which a total of 20 through-holes (first openings) for supplying the resin A to the second cylinder and a total of 20 through-holes (second openings) for supplying the resin B to the second cylinder are provided. However, the number of through-holes is not limited in particular, and may be N (N is a natural number).

In each embodiment described above, an example has been described in which a half of the number of through-holes (first openings) for supplying the resin A to the second cylinder and a half of the number of through-holes (second openings) for supplying the resin B to the second cylinder are communicated with the resin supply path, and the other halves of the respective numbers of through-holes are communicated with the resin discharge path. However, the present invention is limited thereto. In a case where the number of through-holes (first openings) for supplying the resin A to the second cylinder is defined as N (N is a natural number), it is sufficient that: m (m is a natural number smaller than N) through-holes are communicated with the resin supply path; and the remaining (N−m) through-holes are communicated with the resin discharge path. In this case, it is sufficient that: among the N through-holes (second openings) for supplying the resin B to the second cylinder, m through-holes are communicated with the resin discharge path; and the remaining (N−m) through-holes are communicated with the resin supply path. In a case where N is an even number and m is N/2, the number of through-holes communicated with the resin supply path is equal to the number of through-holes communicated with the resin discharge path, and thus, the resin mixing proportion can be adjusted in a range of 0 to 100%. In a case where m is not N/2, the adjustable range of the mixing proportion is narrowed, but the mixing proportion can be adjusted in a limited range. For example, in a case where the number of through-holes for supplying the resin A is 10, the number of through-holes for discharging the resin A is 5, the number of through-holes for supplying the resin B is 5, and the number of through-holes for discharging the resin B is 10, the mixing proportion between the resin A and the resin B can be adjusted in a range of 10:0 to 5:5.

In each embodiment described above, the supply paths provided in the valve case are configured to have lengths that allow the respective supply paths to be communicated with a half of the number of through-holes (first openings) for supplying the resin A to the first cylinder and with a half of the number of through-holes (second openings) for supplying the resin B to the first cylinder. However, the present invention is not limited thereto. In a case where the total number of through-holes (first openings) for supplying the resin A to the first cylinder and the total number of through-holes (second openings) for supplying the resin B to the first cylinder are each N (N is a natural number), it is sufficient that the number of through-holes to which each supply path in the valve case can supply the corresponding resin is less than N.

The flexible tube obtainable by the production apparatus according to each embodiment described above has a structure in which the surface of the blade is covered with a resin layer, wherein the resin layer covering the blade is formed by a mixture of two kinds of resins that are different from each other. As described above, with the flexible tube production apparatus according to the present invention, through control of the distribution ratio (the ratio between the amount of resin to be supplied to the mixing valve and the amount of resin to be discarded) of each of the two kinds of resins, the mixing ratio can be made gradually varied. Accordingly, the mixing ratio of the two kinds of resins forming the resin layer is made varied continuously, not stepwise, from one end to the other end of the flexible tube. Therefore, in the flexible tube obtainable by the production apparatus according to the present invention, the hardness can be made gradually varied, without being suddenly changed in association with change in the resin ratio.

The present invention can be used as a production apparatus for a catheter shaft to be used in producing a medical catheter and for a flexible tube to be used in an endoscope.

As presented above, the embodiments have been described as examples of the technology according to the present disclosure. For this purpose, the accompanying drawings and the detailed description are provided.

Therefore, components in the accompanying drawings and the detailed description may include not only components essential for solving problems, but also components that are provided to illustrate the above described technology and are not essential for solving problems. Therefore, such inessential components should not be readily construed as being essential based on the fact that such inessential components are shown in the accompanying drawings or mentioned in the detailed description.

Further, the above described embodiments have been described to exemplify the technology according to the present disclosure, and therefore, various modifications, replacements, additions, and omissions may be made within the scope of the claims and the scope of the equivalents thereof.

What is claimed is:

1. A flexible tube production apparatus configured to mold a flexible tube by extruding a resin on a surface of a raw material tube, the flexible tube production apparatus comprising:
   a die that has an insertion hole through which the raw material tube is inserted, and an extrusion hole through which a resin is extruded onto the raw material tube passing through the insertion hole;
   a first extruder configured to eject a first resin at a constant speed;
   a second extruder configured to eject a second resin different from the first resin at a constant speed; and
   a mixing valve that has a resin supply path for supplying a resin to the die and a resin discharge path for discharging the resin to outside, the mixing valve being capable of mixing the resins ejected from the first extruder and the second extruder and supplying the resultant resin to the die through the resin supply path, wherein
   the mixing valve includes:
      a first valve configured to distribute the first resin supplied from the first extruder, to the resin supply path and the resin discharge path; and
      a second valve configured to distribute the second resin supplied from the second extruder, to the resin supply path and the resin discharge path,
   the mixing valve increases or decreases a mixing proportion between the first resin and the second resin in association with molding of the flexible tube, by changing a distribution ratio of the first resin in the first valve and a distribution ratio of the second resin in the second valve while keeping at a constant amount a total of a supply amount of the first resin from the first valve to the resin supply path and a supply amount of the second resin from the second valve to the resin supply path,
   the mixing valve is a single valve having a valve body and a case, the valve body having a columnar shape and rotatable about a central axis thereof, the case having an inner peripheral surface slidable relative to an outer peripheral surface of the valve body, the case housing inside the inner peripheral surface the valve body so as to allow the valve body to rotate in a sliding manner,
   both the first valve and the second valve are formed by the same valve body and by the same case,
   in a portion of the valve body, N first openings arranged at an equal angle in a circumferential direction of the valve body are provided in the outer peripheral surface of the valve body, N being a natural number,
   in another portion of the valve body, N second openings each having an identical shape to that of the first opening and arranged at an equal angle in the circumferential direction are provided in the outer peripheral surface of the valve body,
   of the first openings, m first openings that are consecutive in the circumferential direction are communicated with the resin supply path, m being a natural number smaller than N, and first openings that remain, upon subtracting the m first openings from the N first openings, and are consecutive to the m first openings are communicated with the resin discharge path,
   of the second openings, m second openings that are consecutive in the circumferential direction are communicated with the resin discharge path, and second openings that remain, upon subtracting the m second openings from the N second openings, and are consecutive to the m second openings are communicated with the resin supply path,
   the case is provided with:
      a first supply part capable of supplying the first resin ejected from the first extruder, to n first openings, n being a natural number smaller than N; and
      a second supply part capable of supplying the second resin ejected from the second extruder, to n second openings, and
   a sum of the number of first openings communicated with both the first supply part and the resin supply path and the number of second openings communicated with both the second supply part and the resin supply path is n.

2. The flexible tube production apparatus according to claim 1, wherein the number of the first openings communicated with the resin supply path, the number of the first openings communicated with the resin discharge path, and the number of the first openings to which the first supply part supplies the first resin are equal to one another, and the number of the second openings communicated with the resin supply path, the number of the second openings communicated with the resin discharge path, and the number of the second openings to which the second supply part supplies the second resin are equal to one another.

3. The flexible tube production apparatus according to claim 1, further comprising a resin mixing portion configured to mix the first resin and the second resin together, the resin mixing portion being provided at a junction of: a flow path through which the first resin is supplied from the first valve to the die; and a flow path through which the second resin is supplied from the second valve to the die, or to the die side relative to the junction.

4. A flexible tube production apparatus configured to mold a flexible tube by extruding a resin on a surface of a raw material tube, the flexible tube production apparatus comprising:

a die that has an insertion hole through which the raw material tube is inserted, and an extrusion hole through which a resin is extruded onto the raw material tube passing through the insertion hole;

a first extruder configured to eject a first resin at a constant speed;

a second extruder configured to eject a second resin different from the first resin at a constant speed; and a mixing valve that has a resin supply path for supplying a resin to the die and a resin discharge path for discharging the resin to outside, the mixing valve being capable of mixing the resins ejected from the first extruder and the second extruder and supplying the resultant resin to the die through the resin supply path, wherein the mixing valve includes:

a first valve configured to distribute the first resin supplied from the first extruder, to the resin supply path and the resin discharge path; and a second valve configured to distribute the second resin supplied from the second extruder, to the resin supply path and the resin discharge path, the mixing valve increases or decreases a mixing proportion between the first resin and the second resin in association with molding of the flexible tube, by changing a distribution ratio of the first resin in the first valve and a distribution ratio of the second resin in the second valve while keeping at a constant amount a total of a supply amount of the first resin from the first valve to the resin supply path and a supply amount of the second resin from the second valve to the resin supply path, wherein the mixing valve includes:

a first valve body having a columnar shape and rotatable about a central axis thereof;

a first case having an inner peripheral surface slidable relative to an outer peripheral surface of the first valve body, the first case housing inside the inner peripheral surface the first valve body so as to allow the first valve body to rotate in a sliding manner;

a second valve body having a columnar shape and rotatable about a central axis thereof; and a second case having an inner peripheral surface slidable relative to an outer peripheral surface of the second valve body, the second case housing inside the inner peripheral surface the second valve body so as to allow the second valve body to rotate in a sliding manner;

the first valve is formed by the first valve body and the first case, and the second valve is formed by the second valve body and the second case, in the first valve body, N first openings arranged at an equal angle in a circumferential direction of the first valve body are provided in the outer peripheral surface of the first valve body, N being a natural number, in the second valve body, N second openings each having an identical shape to that of the first opening and arranged at an equal angle in a circumferential direction of the second valve body are provided in the outer peripheral surface of the second valve body, of the first openings, m first openings that are consecutive in the circumferential direction are communicated with the resin supply path, m being a natural number smaller than N, and first openings that remain, upon subtracting the m first openings from the N first openings, and are consecutive to the m first openings are communicated with the resin discharge path, of the second openings, m second openings that are consecutive in the circumferential direction are communicated with the resin discharge path, and second openings that remain, upon subtracting the m second openings from the N second openings, and are consecutive to the m second openings are communicated with the resin supply path, the first case is provided with a first supply part capable of supplying the first resin ejected from the first extruder, to n first openings, n being a natural number smaller than N, the second case is provided with a second supply part capable of supplying the second resin ejected from the second extruder, to n second openings, and a sum of the number of first openings communicated with both the first supply part and the resin supply path and the number of second openings communicated with both the second supply part and the resin supply path is n.

5. The flexible tube production apparatus according to claim 4, wherein the number of the first openings communicated with the resin supply path, the number of the first openings communicated with the resin discharge path, and the number of the first openings to which the first supply part supplies the first resin are equal to one another, and the number of the second openings communicated with the resin supply path, the number of the second openings communicated with the resin discharge path, and the number of the second opening to which the second supply part supplies the second resin are equal to one another.

6. The flexible tube production apparatus according to claim 4, further comprising a resin mixing portion configured to mix the first resin and the second resin together, the resin mixing portion being provided at a junction of: a flow path through which the first resin is supplied from the first valve to the die; and a flow path through which the second resin is supplied from the second valve to the die, or to the die side relative to the junction.

\* \* \* \* \*